US009567265B2

(12) United States Patent
Slowing et al.

(10) Patent No.: US 9,567,265 B2
(45) Date of Patent: Feb. 14, 2017

(54) CATALYSTS AND METHODS OF USING THE SAME

(71) Applicant: Iowa State University Research Foundation, Inc., Ames, IA (US)

(72) Inventors: Igor Ivan Slowing, Ames, IA (US); Kapil Kandel, Webster, TX (US)

(73) Assignee: Iowa State University Research Foundation, Inc., Ames, IA (US)

( * ) Notice: Subject to any disclaimer, the term of this patent is extended or adjusted under 35 U.S.C. 154(b) by 431 days.

(21) Appl. No.: 14/015,206

(22) Filed: Aug. 30, 2013

(65) Prior Publication Data

US 2014/0155670 A1   Jun. 5, 2014

Related U.S. Application Data

(63) Continuation-in-part of application No. 13/691,181, filed on Nov. 30, 2012.

(51) Int. Cl.
*C07C 1/22* (2006.01)
*B01J 23/745* (2006.01)
*C07C 1/207* (2006.01)
*B01J 37/10* (2006.01)
*B01J 21/08* (2006.01)
*B01J 23/755* (2006.01)
*B01J 23/881* (2006.01)
*B01J 23/89* (2006.01)
*B01J 29/03* (2006.01)
*B01J 35/00* (2006.01)
*B01J 35/10* (2006.01)
*B01J 37/00* (2006.01)
*B01J 37/02* (2006.01)
*B01J 37/18* (2006.01)

(52) U.S. Cl.
CPC .............. *C07C 1/22* (2013.01); *B01J 21/08* (2013.01); *B01J 23/745* (2013.01); *B01J 23/755* (2013.01); *B01J 23/881* (2013.01); *B01J 23/8906* (2013.01); *B01J 29/0308* (2013.01); *B01J 35/002* (2013.01); *B01J 35/006* (2013.01); *B01J 35/0013* (2013.01); *B01J 35/1019* (2013.01); *B01J 35/1042* (2013.01); *B01J 35/1061* (2013.01); *B01J 37/0018* (2013.01); *B01J 37/0201* (2013.01); *B01J 37/0207* (2013.01); *B01J 37/10* (2013.01); *C07C 1/2078* (2013.01); *B01J 37/18* (2013.01); *C07C 2521/08* (2013.01); *C07C 2523/745* (2013.01); *C07C 2523/755* (2013.01); *Y02P 20/52* (2015.11); *Y02P 20/588* (2015.11)

(58) Field of Classification Search
CPC ............. B01J 23/00; B01J 23/74; B01J 23/76; B01J 23/745; C12N 11/00; C07C 1/20; C07C 1/22

USPC ........ 75/252, 370; 502/64, 66, 71, 258, 260, 502/263; 585/638, 640, 639, 64, 641
See application file for complete search history.

(56) References Cited

U.S. PATENT DOCUMENTS

| | | | |
|---|---|---|---|
| 4,279,756 A | 7/1981 | Weiss et al. | |
| 4,554,390 A | 11/1985 | Curtain et al. | |
| 7,550,634 B2* | 6/2009 | Yao | C10L 1/08 208/142 |
| 7,625,490 B2 | 12/2009 | Cort | |
| 8,039,682 B2* | 10/2011 | McCall et al. | C10G 3/46 585/240 |
| 8,226,740 B2* | 7/2012 | Chaumonnot | C01B 39/48 502/258 |
| 8,361,623 B2 | 1/2013 | Lin et al. | |
| 8,435,912 B2* | 5/2013 | Chaumonnot | 502/158 |
| 8,828,705 B1 | 9/2014 | Lin et al. | |
| 2006/0018966 A1 | 1/2006 | Lin et al. | |
| 2006/0154069 A1 | 7/2006 | Lin et al. | |
| 2008/0021232 A1 | 1/2008 | Lin et al. | |
| 2008/0072705 A1 | 3/2008 | Chaumonnot et al. | |
| 2008/0175783 A1 | 7/2008 | Park et al. | |
| 2009/0283442 A1 | 11/2009 | Mccall et al. | |
| 2010/0133147 A1 | 6/2010 | Chaumonnot et al. | |
| 2010/0196971 A1 | 8/2010 | Lin et al. | |
| 2014/0155669 A1 | 6/2014 | Slowing et al. | |

FOREIGN PATENT DOCUMENTS

| | | |
|---|---|---|
| JP | 2006-069824 A | 3/2006 |
| WO | WO-01/32308 A1 | 5/2001 |
| WO | WO-2004/054708 A2 | 7/2004 |
| WO | WO-2008/060571 A2 | 5/2008 |
| WO | WO-2009/017425 A1 | 2/2009 |
| WO | WO-2010/088001 A2 | 8/2010 |
| WO | WO-2010/088001 A3 | 12/2010 |

OTHER PUBLICATIONS

"U.S. Appl. No. 12/698,656, Notice of Allowance mailed Sep. 18, 2012", 10 pgs.
"U.S. Appl. No. 12/698,656, Preliminary Amendment mailed Apr. 12, 2010", 6 pgs.
"U.S. Appl. No. 12/698,656, Response filed Aug. 22, 2012 to Restriction Requirement mailed May 31, 2012", 7 pgs.
"U.S. Appl. No. 12/698,656, Restriction Requirement mailed May 31, 2012", 11 pgs.
"U.S. Appl. No. 13/300,343, Non Final Office Action mailed Jul. 3, 2013", 8 pgs.
"U.S. Appl. No. 13/300,343, PTO Response to Rule 312 Communication mailed Jul. 29, 2014", 2 pgs.
"U.S. Appl. No. 13/300,343, Response filed Mar. 14, 2013 to Restriction Requirement mailed Feb. 21, 2013", 7 pgs.

(Continued)

*Primary Examiner* — Sharon Pregler
(74) *Attorney, Agent, or Firm* — Schwegman Lundberg & Woessner, P.A.

(57) ABSTRACT

The present invention provides a catalyst including a mesoporous silica nanoparticle and a catalytic material comprising iron. In various embodiments, the present invention provides methods of using and making the catalyst. In some examples, the catalyst can be used to hydrotreat fatty acids or to selectively remove fatty acids from feedstocks.

14 Claims, 16 Drawing Sheets

(56) References Cited

OTHER PUBLICATIONS

"U.S. Appl. No. 13/300,343, Response filed Sep. 12, 2013 to Non Final Office Action mailed Jul. 3, 2013", 9 pgs.
"U.S. Appl. No. 13/300,343, Restriction Requirement mailed Feb. 21, 2013", 9 pgs.
"U.S. Appl. No. 13/691,181, Restriction Requirement mailed Aug. 17, 2015", 10 pgs.
"International Application Serial No. PCT/US2010/000289, International Preliminary Report on Patentability mailed Aug. 11, 2011", 20 pgs.
"International Application Serial. No. PCT/US2010/000289, International Search Report mailed Sep. 14, 2010", 9 pgs.
"International Application Serial No. PCT/US2010/000289, International Search Report mailed Oct. 22, 2010", 9 pgs.
"International Application Serial No. PCT/US2010/000289, Invitation to Pay Additional Fee mailed Jun. 21, 2010", 13 pgs.
"International Application Serial No. PCT/US2010/000289, Written Opinion mailed Sep. 14, 2010", 18 pgs.
"International Application Serial No. PCT/US2010/000289, Written Opinion mailed Oct. 22, 2010", 18 pgs.
Bargiel, J. T., "Commercialization of Lateral Displacement Array for Dewatering of Microalgae", Submitted in partial fulfillment of the requirements for the degree of Master of Science Thesis Committee: Robert Brown, Ph.D. J. Kevin Berner, Ph.D. Edward Caner Cyrus Taylor, Ph.D. Christopher Lane, Ph.D. Department of Physics Case Western Reserve Univer, (May 2009), 53 pgs.
Capasso, J. M., et al., "A colorimetric assay for determination of cell viability in algal cultures", *Biomolecular Engineering*, 20(Issues 4-6), (2003), 4-6.
Cazin, C. S. J., et al., "Versatile Methods for the Synthesis of Si(OR)$_3$ -Functionalised Imidazolium Salts, Potential Precursors for Heterogeneous NHC Catalysts and Composite Materials", *Synthesis* 2005, No. 4, (2005), 622-626.
Cha, S., et al., "Colloidal Graphite-Assisted Laser Desorption/Ionization Mass Spectrometry and MSn of Small Molecules. 1. Imaging of Cerebrosides Directly from Rat Brain Tissue", *Analytical Chemistry*, 79(6), (2007), 2373-2385.
Chan, W. C, et al., "Quantum dot bioconjugates for ultrasensitive nonisotopic detection", *Science*, 281(5385), (Sep. 25, 1998), 2016-2018.
Chen, Y. M., et al., "Flotation removal of algae from water", *Colloids and Surfaces B: Biointerfaces*, 12(1), (Oct. 15, 1998), 49-55.
Chisti, Y., "Biodiesel from microalgae", *Biotechnology Advances*, 25, (2007), 294-306.
Dayananda, C., et al., "Autotrophic cultivation of *Botryococcus braunii* for the production of hydrocarbons and exopolysaccharides in various media", *Biomass & Bioenergy*, 31, (2007), 87-93.
Divakaran, Ravi, et al., "Flocculation of algae using chitosan", *Journal of Applied Phycology*, 14(5), (2002), 419-422.
Doadrio, J. C., et al., "Functionalziation of mesoporous materials with long alkyl claims as a strategy for controlling drug delivery pattern", *Journal of Material Chemistry*, 16, (2006), 462-466.
Doyle, P. S, et al., "Self-assembled magnetic matrices for DNA separation chips.", *Science*, 295(5563), (Mar. 22, 2002), 2237.
Gadenne, B., et al., "Supported ionic liquids ordered mesoporous silicas containing covalently linked ionic species", *Chemical Communications*, 15, (2004), 1768-1769.
Giri, Supratim, et al., "Stimuli-Responsive Controlled-Release Delivery System Based on Mesoporous Silica Nadorods Capped with Magnetic Nanoparticles", *Angew. Chem. Int. Ed.* 2005, 44, (2005), 5038-5044.
Gu, H., et al., "Using Biofunctional Magnetic Nanoparticles to Capture Vancomycin-Resistant Enterococci and Other Gram-Positive Bacteria at Ultralow Concentration", *J. Am. Chem. Soc.*, 125(51), (2003), 15702-15703.
Hall, S. R., et al., "Template-directed synthesis of bi-functionalized organo-MCM-41 and phenyl-MCM-48 silica mesophases", *Chem. Commun.*, (1999), 201-202.

Herrero, M. A., et al., "Recent Advances in the Covalent Functionalization of Carbon Nanotubes", *Mol. Cryst. Liq. Cryst.*, 483, (2008), 21-32.
Hirsch, A., et al., "Functionalization of Carbon Nanotubes", *Topics in Current Chemistry—Functional Molecular Nanostructures*, vol. 245, (2005), 193-237.
Hung, Yung-Tse, et al., "Algae Harvest Energy Conversion", *Handbook of Environmental Engineering*, vol. 11: *Environmental Bioengineering*, (2010), 723-741.
Kim, T.-W., et al., "Structurally Ordered Mesoporous Carbon Nanoparticles as Transmembrane Delivery Vehicle in Human Cancer Cells", *Nano Letters*, 8(11), (2008), 3724-3727.
Leon-Banares, R., et al., "Transgenic microalgae as green cell-factories", *Trends in Biotechnology*, 22(1), (2004), 45-52.
Linton, P., et al., "Growth and Morphology of Mesophorous SBA-15 Particles", *Chem. Mater.*, 20, (Apr. 10, 2008), pp. 2878-2880.
MacQuarrie, D. J, "Organically modified hexagonal mesoporous silicas—Clean of high loading and non-catalytic second groups on catalytic activity of amine-derivatised materials", *Green Chemistry*, vol. 1, No. 4, DDOI: 10.1039/a904692e, (Sep. 6, 1999), 195-198.
Middlebrooks, E. J., et al., "Techniques for Algae Removal from Wastewater Stabilization Ponds", *Journal (Water Pollution Control Federation)*, 46(12), (Dec. 1974), 2676-2695.
Nepal, D., et al., "Chapter 4—Functionalization of Carbon Nanotubes", *Functional Nanomaterials*, Geckeler, K. E., et al., Editors, American Scientific Publishers, (2006), 57-79.
Pan, C., et al., "Carbon Nanotubes as Adsorbent of Solid-Phase Extraction and Matrix for Laser Desorption/Ionization Mass Spectrometry", *J. Am. Soc. Mass Spectrom.*, 16, (2005), 263-270.
Pan, C., et al., "Using Oxidized Carbon Nanotubes as Matrix for Analysis of Small Molecules by MALDI-TOF MS", *J. Am. Soc. Mass Spectrom.*, 16, (2005), 883-892.
Soeng, H., "Controlling the Selectivity of Competitive Nitroaldol Condensation by Using Bifunctionalized Mesoporous silica Nanosphere-Based Catalytic System", *Journal of the American Chemical Society*, vol. 126, No. 4, (Sep. 1, 2004), 1010-1011.
Udayakumar, S., et al., "Imidazolium derivatives functionalized MCM-41 for catalytic conversion of carbon dioxide to cyclic carbonate", *Catalysis Communications*, 10(5), (2009), 659-664.
Uduman, N., et al., "Dewatering of microalgal cultures: A major bottleneck to algae-based fuels", *Journal of Renewable and Sustainable Energy*, 2, (2010), 012701-15.
Van Meter, D. S., et al., "Characterization of surface-confined ionic liquid stationary phases: impact of cation and anion identity on retention", *Analytical and Bioannalytical Chemistry* 393(1), (2008), 283-294.
Wang, J., et al., "Superparamagnetic Fe$_2$O$_3$Beads-CdSe/ZnS Quantum Dots Core-Shell Nanocomposite Particles for Cell Separation", *Nano Lett.*, 4(31 (2004), 409-413.
Xu, C., et al., "Dopamine as a Robust Anchor to Immobilize Functional Molecules on the Iron Oxide Shell of Magnetic Nanoparticles", *J. Am. Chem. Soc.*, 126(32), (2004), 9938-9939.
Yiu, H H P, et al., "Synthesis of novel magnetic iron metal-silica (Fe—SBA-15) and magnetite-silica (Fe$_3$O$_4$-SBA-15) nanocomposites with a high iron content using temperature-programed reduction", *Nanotechnology* 19, (2008), 7 pgs.
Zhang, H., et al., "Colloidal Graphite-Assisted Laser Desorption/Ionization MS and MSn of Small Molecules. 2. Direct Profiling and MS Imaging of Small Metabolites from Fruits", *Analytical Chemistry*, 79(17), (2007), 6575-6584.
Zhang, X., et al., "Harvesting algal biomass for biofuels using ultrafiltration membranes.", *Bioresour Technol.*, 101(14), (Jul. 2010), 5297-304.
Zheng, L., et al., "Magnetic Hollow Spheres of Periodic Mesoporous Organosilica and Fe3O4 Nanocrystals: Fabricaion and Structure Control", *Advanced Materials*, 20(4), (2008), 805-809.
Zhila, N. O., et al., "Effect of Nitrogen Limitation on the Growth and Lipid Composition of the Green Alga *Bobyococcus braunii* Kütz IPPAS H-252", *Russian Journal of Plant Physiology*, 52(3), (2005), 311-319.
"U.S. Appl. No. 13/691,181, Non Final Office Action mailed Jun. 16, 2016", 10 pgs.

(56) References Cited

OTHER PUBLICATIONS

"U.S. Appl. No. 13/691,181, Response filed Mar. 2, 2016 to Restriction Requirement mailed Jan. 13, 2016", 25 pgs.
"U.S. Appl. No. 13/691,181, Restriction Requirement mailed Jan. 13, 2016", 6 pgs.

* cited by examiner

CATALYSTS AND METHODS OF USING THE SAME

CROSS-REFERENCE TO RELATED APPLICATIONS

This application is a continuation-in-part of and claims the benefit of priority under 35 U.S.C. §120 to U.S. Utility application Ser. No. 13/691,181 entitled "ADSORBENT CATALYTIC NANOPARTICLES AND METHODS OF USING THE SAME," filed Nov. 30, 2012, the disclosure of which is incorporated herein in its entirety by reference.

STATEMENT OF GOVERNMENT SUPPORT

This invention was made with Government support under contract no. DE-AC02-07CH11358 awarded by the U.S. Department of Energy. The U.S. Government has certain rights in this invention.

BACKGROUND OF THE INVENTION

Petroleum-derived solvents and fuels are of environmental concern and are under legislation to be replaced by biorenewable substitutes that afford reduced environmental impact. Unpredictable petroleum prices and the increasing desire for energy independence and security have led to burgeoning research activities directed toward developing a variety of alternative fuels. Among these new fuels, biodiesel is a biorenewable, nontoxic diesel that can be produced by transesterification of various oil feedstocks, including vegetable oils, animal fats, algal oils, and restaurant waste oils. Examples of biodiesel can include fatty acid $C_{1-5}$ alkyl esters, such as soy diesel (methyl soyate), rapeseed methyl ester, and various vegetable and animal fat methyl esters. Another new fuel is green diesel or renewable diesel, produced by hydrotreatment of various oils to produce a hydrocarbon mixture. Green diesel can be chemically identical to petroleum-derived fuels.

Catalysts are essential materials in a wide variety of useful and important chemical reactions, such as hydrotreatment. Many catalysts lack selectivity Generally, catalysts are unselectively exposed to materials in a chemical reaction. Therefore, a molecule at lower concentration with a particular reactivity with the catalyst has a lower chance of undergoing the chemical change caused by the catalyst than a different molecule at a higher concentration having the same reactivity with the catalyst.

SUMMARY OF THE INVENTION

In various embodiments, the present invention provides a method including combining a catalyst with at least one first molecule. The catalyst includes a mesoporous silica nanoparticle comprising a catalytic material including iron. The at least one first molecule includes at least one of a fatty acid, a fatty acid ester, a monoglyceride, a diglyceride, and a triglyceride. The combining provides a mixture. The method also includes combining the mixture with a hydrogen gas under conditions so that the catalytic material in the catalyst catalyzes a chemical transformation of the first molecule.

In various embodiments, the present invention provides a method including combining an adsorbent catalyst with at least one first molecule including at least one of a fatty acid, a fatty acid ester, a monoglyceride, a diglyceride, and a triglyceride, to provide a mixture. The adsorbent catalyst includes a mesoporous silica nanoparticle comprising a catalytic material including iron and at least one adsorbent functional group including a functional group selected from the group consisting of an amino($C_1$-$C_{20}$)alkyl group or a salt thereof, a ($C_1$-$C_{20}$)alkyl carboxylic acid group or a salt thereof, a ($C_1$-$C_{20}$)alkyl sulfonic acid group or a salt thereof, and a perfluoro($C_1$-$C_{20}$)alkyl group. The alkyl unit of the aminoalkyl group, the alkyl carboxylic acid group, the alkyl sulfonic acid group, and of the perfluoroalkyl group is covalently bound to the mesoporous silica nanoparticle. The $C_1$-$C_{20}$ alkyl groups of the amino($C_1$-$C_{20}$)alkyl group are independently optionally interrupted by one or two —NH— groups.

In various embodiments, the present invention provides a catalyst including a mesoporous silica nanoparticle. The catalyst also includes a catalytic material including iron nanoparticles. The iron nanoparticles are at least partially within pores of the mesoporous silica nanoparticle.

In various embodiments, the present invention provides a catalyst including a mesoporous silica nanoparticle having a particle size of about 50 nm to about 1200 nm, a pore size of about 5 nm to about 15 nm, and a pore volume of about 0.5 to about 1.5 cm$^3$/g. The catalyst also includes a catalytic material including iron nanoparticles. The iron nanoparticles have a particle size of about 5 nm to about 15 nm. The iron nanoparticles are at least partially within pores of the mesoporous silica nanoparticle. The iron nanoparticles are about 1-10 wt % of the catalyst. The catalyst has a surface area of about 150 m$^2$/g to about 375 m$^2$/g.

Various embodiments of the present invention provide advantages over other mesoporous silica nanoparticles and methods of using the same, including some advantages that are unexpected. In some embodiments, as compared to other catalysts, the catalyst can provide greater catalytic activity in chemical transformations of molecules such as fatty acids, fatty acid esters, monoglycerides, diglycerides, and triglycerides. In some embodiments, the catalyst can give a greater selectivity for catalyzing particular hydrotreatment reactions over other hydrotreatment reactions, such as of fatty acids, as compared to other hydrotreatment catalysts. Various embodiments of the catalyst allow better control over the product distribution of hydrotreatment, such as of fatty acids, than other catalysts, providing a hydrocarbon product (e.g., green diesel) that is more easily and more efficiently used than other hydrotreatment products. In various embodiments, the catalyst can be provided with a lower cost than other hydrotreatment catalysts. In various embodiments, the catalyst can provide various advantages at lower cost than available from other catalysts or methods, such as lower cost of controlling hydrotreatment product distribution, and lower cost for a achieving a given hydrotreatment reaction rate. In some embodiments, the catalyst can provide an economical, efficient and sulfur-free method for converting microalgal oil into green diesel.

Various embodiments of the catalyst allow better control over the product distribution of hydrotreatment, such as of fatty acids, than other catalysts, providing a hydrocarbon product (e.g., green diesel) that is more easily and more efficiently used than biodiesel. For example, green diesel can have less oxygen atoms than biodiesel, or no oxygen atoms, giving the green diesel higher energy density that biodiesel. For example, green diesel can have less unsaturated hydrocarbons than biodiesel, or no unsaturated hydrocarbons, which can result in greater storage stability and less likelihood of oxidation and degradation over time than biodiesel. For example, the heat of combustion of green diesel can be higher than the heat of combustion than biodiesel.

In various embodiments of an adsorbent catalyst, the combination of the ability to not only separate particular substances from a mixture but also to catalyze the chemical transformation of those substances is unique and advantageous. In some embodiments, the proximity of the adsorbent functional groups and the catalytic material in the adsorbent catalyst yields desirable or advantageous and unexpected properties.

For example, the combination of adsorbent functional groups on the adsorbent catalyst and catalytic materials therein can cause molecules that are adsorbed by the adsorbent groups to be subjected to the catalytic material differently than molecules that are not adsorbed by the adsorbent groups. In some embodiments, the adsorbent functional groups can selectively adsorb a certain molecule or class of molecule from a mixture of molecules; thus, in various examples, the adsorbent catalyst can selectively expose certain molecules or classes of molecules to the catalytic material, thereby selectively causing a chemical transformation catalyzed by the catalytic material or influencing the selectivity thereof.

In some embodiments, the selectivity of a particular adsorbent catalyst toward various chemical reactions of a molecule adsorbable by the adsorbent groups can be different when the molecule is adsorbed to an adsorbent group on the nanoparticle, versus when the molecule is not adsorbed to an adsorbent group on the nanoparticle. Thus, in various embodiments, the selectivity of the chemical reactions of a first molecule catalyzed by the catalytic material can be advantageously modulated by allowing the adsorbent groups to adsorb the first molecule prior to subjecting the first molecule and the adsorbent catalyst to conditions so that the catalytic material catalyzes a chemical transformation of the first molecule.

In some examples, by allowing an adsorbent catalyst including a hydrotreatment catalyst to first adsorb a fatty acid from a mixture, and then subjecting the adsorbent catalyst with the adsorbed fatty acid to conditions effective for the catalytic material to catalyze hydrotreatment, the products formed can advantageously and unexpectedly have a higher C:O ratio than can be achieved when the fatty acid is hydrotreated using the catalytic material but with the catalytic material not having selectively adsorbent groups proximate thereto. In some examples, by allowing an adsorbent catalyst including a hydrotreatment catalyst to first adsorb a fatty acid from a mixture, and then subjecting the adsorbent catalyst with the adsorbed fatty acid to conditions so that the catalytic material catalyzes hydrotreatment, the selectivity of the hydrotreatment toward hydrodeoxygenation can be higher as compared to the cracking and decarboxylation than can be achieved when the fatty acid is hydrotreated using the catalytic material but not having selectively adsorbent groups proximate thereto, thereby yielding an increased average hydrocarbon length of the resulting product mixture; thus, various embodiments produce hydrocarbon mixtures having higher C:O ratios, higher cetane numbers, with less need for further processing, and/or are formed with less environmentally damaging release of $CO_2$.

In the manufacture of green diesel, fatty acids in the feedstock can form compounds by combining with certain catalytic materials, such as basic transesterification catalysts, to form soaps and consuming catalyst, thus reducing the efficiency of the process. In certain embodiments, the adsorbent catalyst can be used to efficiently remove fatty acids from a green diesel feedstock, and subsequently to conveniently chemically hydrotreat the removed fatty acids, forming hydrocarbon mixtures that can be useful as fuel having better qualities than hydrotreated fatty acids produced by other methods, such as higher C:O ratio, and lower cost. The method of production can have less complexity and less energy use, and allow for the use of cheaper starting materials, such as for bio-diesel production. In certain embodiments, the adsorbent catalyst can be reused multiple times for separation of one or more materials from a mixture and subsequent catalytic conversion of the materials.

BRIEF DESCRIPTION OF THE FIGURES

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION OF THE INVENTION

Figure 1A:
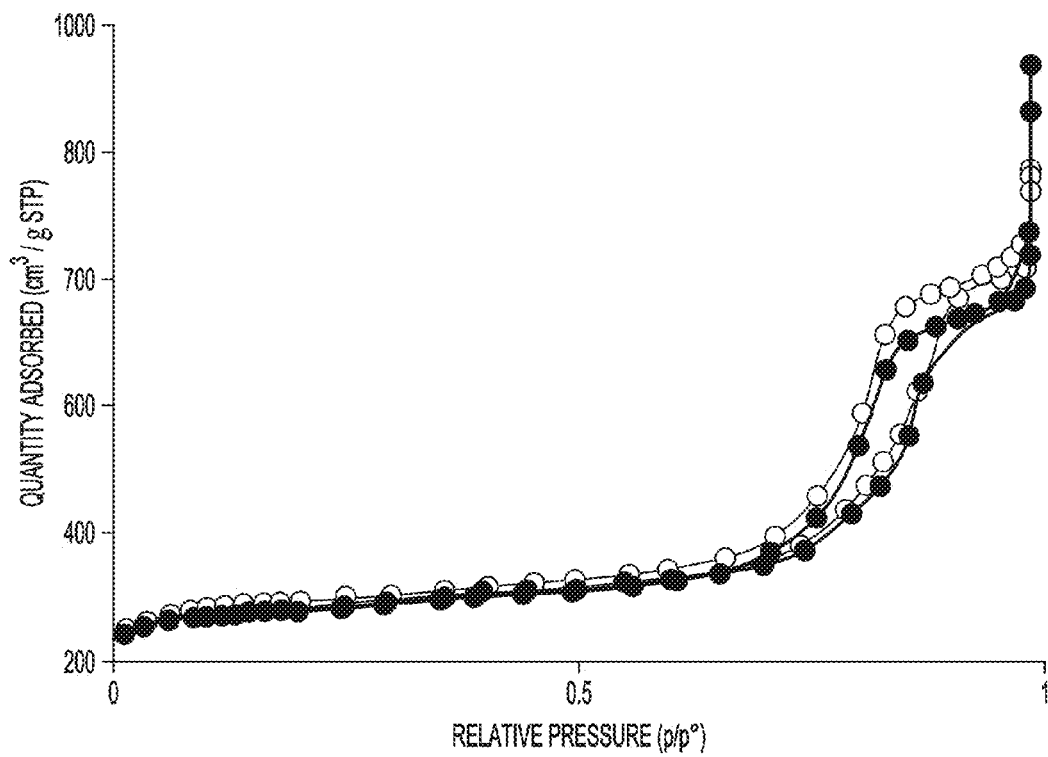
FIG. 1a illustrates $N_2$ sorption isotherms of MSN (open circle) and Fe-MSN (filled circle), in accordance with various embodiments.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods of manufacturing described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

Selected substituents within the compounds described herein are present to a recursive degree. In this context, "recursive substituent" means that a substituent may recite another instance of itself or of another substituent that itself recites the first substituent. Recursive substituents are an intended aspect of the disclosed subject matter. Because of the recursive nature of such substituents, theoretically, a large number may be present in any given claim. One of ordinary skill in the art of organic chemistry understands that the total number of such substituents is reasonably limited by the desired properties of the compound intended. Such properties include, by way of example and not limitation, physical properties such as molecular weight, solubility, and practical properties such as ease of synthesis. Recursive substituents can call back on themselves any suitable number of times, such as about 1 time, about 2 times, 3, 4, 5, 6, 7, 8, 9, 10, 15, 20, 30, 50, 100, 200, 300, 400, 500, 750, 1000, 1500, 2000, 3000, 4000, 5000, 10,000, 15,000, 20,000, 30,000, 50,000, 100,000, 200,000, 500,000, 750,000, or about 1,000,000 times or more.

The term "about" as used herein can allow for a degree of variability in a value or range, for example, within 10%, within 5%, or within 1% of a stated value or of a stated limit of a range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbons or, in some embodiments, from 2 to 8 carbon atoms. Examples include, but are not limited to vinyl, —CH═CH (CH$_3$), —CH═C(CH$_3$)$_2$, —C(CH$_3$)═CH$_2$, —C(CH$_3$)═CH(CH$_3$), —C(CH$_2$CH$_3$)═CH$_2$, cyclohexenyl, cyclopentenyl, cyclohexadienyl, butadienyl, pentadienyl, and hexadienyl among others.

The term "amine" as used herein refers to primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form —NH$_2$, —NHR, —NR$_2$, —NR$_3^+$, wherein each R is independently selected, and protonated forms of each, except for —NR$_3^+$, which cannot be protonated. Accordingly, any compound substituted with an amino group can be viewed as an amine. An "amino group" within the meaning herein can be a primary, secondary, tertiary or quaternary amino group. An "alkylamino" group includes a monoalkylamino, dialkylamino, and trialkylamino group.

The terms "halo" or "halogen" or "halide", as used herein, by themselves or as part of another substituent mean, unless otherwise stated, a fluorine, chlorine, bromine, or iodine atom.

The term "hydrocarbon" as used herein refers to a functional group or molecule that includes carbon and hydrogen atoms. The term can also refer to a functional group or molecule that normally includes both carbon and hydrogen atoms but wherein all the hydrogen atoms are substituted with other functional groups.

The term "pore" as used herein refers to a depression, slit, or hole of any size or shape in a solid object. A pore can run all the way through an object or partially through the object. A pore can intersect other pores.

The term "solvent" as used herein refers to a liquid that can dissolve a solid, liquid, or gas. Nonlimiting examples of solvents are silicones, organic compounds, water, alcohols, ionic liquids, and supercritical fluids.

The term "silica" as used herein refers to silicon dioxide (SiO$_2$) of any particle size, shape, particle size distribution, shape distribution and surface functionality, including chemically treated silicas. It can also refer to a polysiloxane that includes a silicon and oxygen atom network, including at least in part a silicon-oxygen-silicon (silicon atom bonded to oxygen atom bonded to silicon atom) network, wherein the compound can be a polymer of any length or degree of branching. In various embodiments, the network can terminate with an Si═O group, or an Si—OH group. The silica gel or matrix can include polysiloxanes in 30%, 50%, 80%, 90%, 95%, 99%, 99.5%, 99.9%, or in any suitable percent composition (wt %).

The term "room temperature" as used herein refers to a temperature of about 15° C. to 28° C.

The term "contacting" as used herein refers to the act of touching, making contact, or of bringing to immediate or close proximity, including at the molecular level, for example, to bring about a chemical reaction or physical change.

The term "adsorb" or "adsorption" as used herein refers to the binding of a molecule to an adsorbent group on a nanoparticle, wherein the molecule is reversibly or irreversibly bound to the particle. The binding can occur on the outer surface of the particle, including outer surfaces that are within the outer periphery of the particle, including the insides of pores that may be present in the nanoparticle.

The term "algae" as used herein refers to the paraphyletic group of simple, typically autotrophic, photosynthetic organisms, ranging from unicellular (e.g., green algae) to multicellular forms. Suitable algae genera can include *Botryococcus, Chlamydomas, Chlorella, Crypthecodinium, Cyclotella, Cylindrotheca, Dunaliella, Haematococcus, Isochrysis, Monallanthus, Monoraphidium, Nannochloris, Nannochloropsis, Neochloris, Nitzschia, Phaeodactylum, Schizochytrium, Spirulina, Stichococcus, Synechocystis, Tagetes,* and *Tetraselmis*. Specific species can include, for example, *Botryococcus braunii, Chlamydomas perigranulata, Chlorella emorsonii, Chlorella minutissima, Chlorella sorokiniana, Chlorella vulgaris, Crypthecodinium Cohnii, Cyclotella cryptica, Dunaliella Bardawil, Dunaliella salina, Dunaliella primolecta, Haematococcus pluvialis, Isochrysis galbana, Monallanthus salina, Neochloris oleoabundans, Nitzschia closterium, Phaeodactylum tricornutum, Spirulina platensis, Tagetes erecta, Tagetes patula, Tetraselmis suecica,* or *Tetraselmis suecica*. Algea can include any suitable form of algae, including genetically modified algae, e.g., transgenic microalgae, are well known in the art. See, for example, Leon-Banares et al., *Trends in Biotechnology,* 22 (2004) 45-52.

The term "microalgae" as used herein refers to microscopic algae, typically found in freshwater and marine systems, often referred to as microphytes.

As used herein, the term "sequestering" or "sequestration" of a molecule, such as of a fatty acid from a mixture, refers to the process of concentrating a fatty acid. The concentration can occur by, for example, absorbing and/or adsorbing the fatty acid onto or into a nanoparticle. The absorbing or adsorbing can include binding to the surface of the nanoparticle, such as by electrostatic associations, and the like.

The term "nanoparticles" as used herein refers to particles with an average diameter less than about 750 nm. In some embodiments, the particles can be less than about 500 nm, or less than about 300 nm, or approximately 50-200 nm. In some embodiments, nanoparticles can be approximately 75-100 nm in diameter.

The term "mesoporous" as used herein refers to containing pores wherein the pores have a diameter of between about 0.5 nm and about 200 nm, or between about 1 nm and about 100 nm, or between about 2 nm and about 50 nm.

The term "hydrotreatment" as used herein is used to refer to a catalytic process performed in the presence of hydrogen that includes reductive chemical reactions, such as, for example, reduction of unsaturated bonds and reduction of carbon to lesser oxidation states via removal of bonds to oxygen or other heteroatoms, including, for example, carboxylate reduction, carboxylate decarboxylation, carboxylate decarbonylation, alkene reduction, reduction of conjugated or aromatic unsaturated bonds, reduction of any carbon-oxygen bond including, for example, conversion of glycerine to propane, or other reactions including carbon-carbon bond cracking and cycloparaffin formation via cyclization, or cycloparaffin formation via cyclization followed by hydrogenation/saturation of conjugated or nonconjugated C—C bonds, or aromatization. For example, hydrotreatment can include a catalytic process whereby oxygen is removed from organic compounds, for example as water (hydrodeoxygenation); sulfur from organic sulfur compounds, for example as dihydrogen sulfide (hydrodesulfurization); nitrogen from organic nitrogen compounds, for example as ammonia (hydrodenitrogenation); and halogens from organic compounds, for example, as chlorine from organic chloride compounds as hydrochloric acid (hydrodechlorination). Hydrotreating can also include hydrogenation and reduction.

The term "fatty acid" as used herein refers to a carboxylic acid having a long-chain aliphatic hydrocarbon tail, e.g., R—C(O)OH where R is the aliphatic hydrocarbon tail, which can be saturated or unsaturated, and straight-chain, branched, or cyclic. Fatty acids can include short-chain fatty acids, having aliphatic tails of fewer than about 6 carbons, medium-chain fatty acids, having aliphatic tails of about 6-12 carbon atoms, long-chain fatty acids, having aliphatic tails of about 13-21 carbon atoms, and very long chain fatty acids, having aliphatic tails of greater than about 22 carbons. Fatty acids can include any suitable number of carbon atoms, such as about 1 to 50 carbon atoms. Fatty acid esters are esters of fatty acids. A free fatty acid is a fatty acid wherein the acid moiety is in the form of —C(O)OH and not a salt or an ester thereof. Unless otherwise designated, herein the term "fatty acid" refers to a free fatty acid.

The term "triglyceride" as used herein refers to a fatty acid ester of glycerol.

Method of Using a Catalyst Including Mesoporous Silica Nanoparticles and a Catalytic Material.

Various embodiments provide a method including combining a catalyst with at least one first molecule. The catalyst includes a mesoporous silica nanoparticle including a catalytic material including iron. The catalyst can be any suitable catalyst described herein, such as a catalyst having adsorbent functional groups thereon or a catalyst not having adsorbent functional groups thereon. The first molecule can include at least one of a fatty acid, a fatty acid ester, a monoglyceride, a diglyceride, and a triglyceride, to provide a mixture. The method can include combining the mixture with a hydrogen gas under conditions so that the catalytic material in the catalyst catalyzes a chemical transformation of the first molecule.

The chemical transformation of the first molecule can be any suitable chemical transformation. The chemical transformation can be a hydrotreatment of the first molecule. The hydrotreating can occur at any suitable temperature, pressure, and for any suitable time such that the hydrotreating generates suitable hydrotreated material for moving forward in the processing. The hydrotreatment can be any suitable hydrotreatment, and can include at least one of cracking, hydrogenation, reduction, decarboxylation, and hydrodeoxygenation. The method can include controlling the pressure of the hydrogen to be any suitable pressure such that hydrotreating of the first molecule occurs, such as about 1 bar to about 1000 bar, about 10 bar to about 500 bar, about 10 bar to about 300 bar, about 10 bar to about 100 bar, or about 100 to 150 bar. In some embodiments, reactor pressures can be about 25 to 250 bar, and in some embodiments, reactor pressures can be about 60 to 200 bar. The method can include controlling the temperature of the mixture to be any suitable temperature such that hydrotreating of the first molecule occurs, such as about 150° C. to about 1000° C., about 250° C. to about 350° C., about 200° to about 500° C., about 250° to about 450° C., about 300° to about 550° C., about 300° to about 400° C., or about 340° to about 530° C. The duration of the hydrotreatment can be any suitable duration, such as about 1 minute, 5 minutes, 10 minutes, 20 minutes, 30 minutes, 60 minutes, 4 hours, about 8 hours, or more.

Combining the catalyst and the first molecule can be any suitable combining that allows the catalyst and the first molecule to come into contact. The combining of the catalyst with the first molecule can include combining the catalyst with a solution comprising the first molecule, to provide the mixture. The first molecule can be a fatty acid. The method can include combining the catalyst with one or more fatty acids. The fatty acid can be any suitable fatty acid. In some embodiments, the fatty acid is a $C_{5-50}$ fatty acid. The fatty acid can be oleic acid. In some examples, the fatty acid can be an unsaturated fatty acid such as myristoleic acid, palmitoleic acid, sapienic acid, oleic acid, elaidic acid, vaccenic acid, linoleic acid, linoelaidic acid, arachidonic acid, icosapentaenoic acid, erucic acid, docasahexaenoic acid. In some examples, the fatty acid can be a saturated fatty acid such as propionic acid, butyric acid, valeric acid, caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, heptacostylic acid, montanic acid, nonacosylic acid, melissic acid, henatriacontylic acid, lacceroic acid, psyllic acid, geddic acid, ceroplastic acid, or hexatricontylic acid.

The method can include separating the catalyst from the mixture. The method can include at least one of using and selling the separated mixture as a feedstock for generating green diesel.

In some embodiments, when the catalyst is magnetic, the magnetic property can be used to separate the catalyst including the at least one first molecule adsorbed thereto, such as by using a magnetic field. The magnetic field can be generated in any effective method known to one of skill in the art, and can be of any strength sufficient to separate the catalyst from the mixture. The magnetic field can be generated by an electromagnet, a non-electromagnet, or a combination thereof. The magnetic field can originate from a source that is in contact with the media, or from a source that is outside the approximate boundaries of the media. The magnetic field can originate from one or more sources, and multiple sources can be in the same or different locations. The exposure can be sufficient to cause the catalyst to move toward or away from a specific direction. The exposure can be sufficient to cause the catalyst to gather in a specific area. The remainder of the mixture can be transferred away from the catalyst, or the catalyst can be transferred away from the remaining mixture, such as by decanting, draining, centrifuging, siphoning, pumping, gravity, or a combination thereof.

Method of Using a Catalyst Including Mesoporous Silica Nanoparticles and a Catalytic Material, the Catalyst Having Adsorbent Groups Thereon.

Various embodiments of the present invention provide a method including an adsorbent catalyst. The adsorbent catalyst can be any suitable adsorbent catalyst described herein, and the method can be any suitable method of using the catalyst. The adsorbent catalyst can include a mesoporous silica nanoparticle including a catalytic material including iron (e.g., elemental iron or a compound of iron). The adsorbent catalyst can include at least one adsorbent functional group including a functional group selected from the group consisting of an amino($C_1$-$C_{20}$)alkyl group or a salt thereof, a ($C_1$-$C_{20}$)alkyl carboxylic acid group or a salt thereof, a ($C_1$-$C_{20}$)alkyl sulfonic acid group or a salt thereof, and a perfluoro ($C_1$-$C_{20}$)alkyl group, wherein the alkyl unit of the aminoalkyl group, the alkyl carboxylic acid group, the alkyl sulfonic acid group, and of the perfluoroalkyl group is covalently bound to the mesoporous silica nanoparticle, and wherein the $C_1$-$C_{20}$ alkyl groups of the amino ($C_1$-$C_{20}$)alkyl group are independently optionally interrupted by one or two —NH— groups.

The method can include combining at least one adsorbent catalyst with at least one first molecule that is selectively adsorbed by the adsorbent functional group, to provide a mixture. In some examples, the first molecule is a fatty acid. A single adsorbent catalyst can adsorb one or more than one first molecule. In some examples, each adsorbent catalyst can adsorb a quantity of the first molecules equal to about one to the quantity of adsorbent functional groups substituted on the mesoporous silica nanoparticle. Herein, where a first molecule is described, such as the selective adsorption, separation, and reaction thereof, a first family of molecules are also described and included as an embodiment of the present invention. For example, the first family can be fatty acids. Likewise, where a second molecule is described, a second family of molecules is likewise described, such at least one of fatty acid esters and triglycerides.

The method can include combining the mixture with a first reagent, under conditions so that the catalytic material in the adsorbent catalyst catalyzes a chemical transformation of the first molecule. For example, the first reagent can be hydrogen, and the catalytic material can be a hydrotreatment catalyst, such that the catalyzation of the chemical transformation of the first molecule is hydrotreatment of the first molecule. The hydrotreatment can be any suitable hydrotreatment described herein.

In some examples, combining the adsorbent catalyst with the first molecule can include combining the adsorbent catalyst with a solution including the molecule that is selectively adsorbed by the adsorbent functional group, to provide the mixture. The solution can further include at least one second molecule that is at least one of not adsorbed by the adsorbent functional group and adsorbed by the adsorbent functional group at a lower rate than the first molecule is adsorbed by the adsorbent functional group. In some embodiments, the solution can include a solvent. The first molecule can be any suitable mole percent of the mixture. For example, not including a solvent, the first molecule can be about 0.0001 mol % of the mixture or less, or about 0.001, 0.01, 0.1, 1, 2, 3, 4, 5, 10, 15, 20, 40, 60, 80, 90, 95, 96, 97, 98, 99, 99.9, 99.99, 99.999 mol % or more of the mixture. In some examples, the second molecule is at least one of a fatty acid ester and a triglyceride, such as at least one of a $C_{5-50}$ fatty acid $C_{1-50}$ ester and a triglyceride having $C_{5-50}$ fatty acid groups. In some embodiments, the first molecule is a fatty acid such as a $C_{5-50}$ fatty acid. The second molecule can be any suitable mole percent of the mixture. For example, not including a solvent, the first molecule can be about 0.0001 mol % of the mixture or less, or about 0.001, 0.01, 0.1, 1, 2, 3, 4, 5, 10, 15, 20, 40, 60, 80, 90, or about 95 mol % or more of the mixture.

The adsorbent catalyst and the at least one compound can be exposed to one another at any relative concentration, and for any duration of time, sufficient to allow formation of at least some adsorbent catalyst having first molecules adsorbed thereon. For example, the duration of time can be about 1 minute, 5 minutes, 10 minutes, 20 minutes, 30 minutes, 60 minutes, 4 hours, about 8 hours, or more.

In various embodiments, the method can include separating at least some of the adsorbent catalyst from the mixture, including the adsorbent catalyst having the at least one first molecule adsorbed thereto, and optionally additionally including any adsorbent catalyst not having the first molecule adsorbed thereto. In some embodiments, the separated mixture can be at least one of used and sold as a feedstock for generating green diesel. The method can include combining the separated adsorbent catalyst with a first reagent under conditions so that the catalytic material in the adsorbent catalyst catalyzes a chemical transformation of the first molecule. For example, the reagent can include hydrogen gas and the conditions can be any suitable conditions. The method can include controlling the pressure of the hydrogen to be any suitable pressure such that hydrotreating of the first molecule occurs, such as about 1 bar to about 1000 bar, about 10 bar to about 500 bar, about 10 bar to about 300 bar, about 10 bar to about 100 bar, or about 100 to 150 bar. In some embodiments, reactor pressures can be about 25 to 250 bar, and in some embodiments, reactor pressures can be about 60 to 200 bar. The method can include controlling the temperature of the mixture to be any suitable temperature such that hydrotreating of the first molecule occurs, such as about 150° C. to about 1000° C., about 250° C. to about 350° C., about 200° to about 500° C., about 250° to about 450° C., about 300° to about 550° C., about 300° to about 400° C., or about 340° to about 530° C. The duration of the hydrotreatment can be any suitable duration, such as about 1 minute, 5 minutes, 10 minutes, 20 minutes, 30 minutes, 60 minutes, 4 hours, about 8 hours, or more. In some embodiments, the method includes at least one of using and selling the product of the chemical transformation of the first molecule as a fuel, such as a transportation fuel such as gasoline or diesel.

In some embodiments, when the catalyst is magnetic, the magnetic property can be used to separate the catalyst including the at least one first molecule adsorbed thereto, such as by using a magnetic field. The magnetic field can be generated in any effective method known to one of skill in the art, and can be of any strength sufficient to concentrate the adsorbed first molecules. The magnetic field can be generated by an electromagnet, a non-electromagnet, or a combination thereof. The magnetic field can originate from a source that is in contact with the media, or from a source that is outside the approximate boundaries of the media. The magnetic field can originate from one source or multiple sources, and the multiple sources can be in one location or different locations.

The exposure to the magnetic field can be sufficient to concentrate the first molecule or family of molecules. Concentration refers to the amount of first molecules in a given volume of the media, and can refer to any degree of concentration. Concentration can include an at least 0.01%, 5%, 10%, 20%, 40%, 80%, 90%, 95%, 99% increase in the moles of the first molecules in a given volume of the media. Concentrating the first molecules can also include removing the adsorbed first molecules from the media, which corresponds to the given volume of the media approaching zero as the amount of the first molecules remains constant. Concentrating the first molecules can refer to the effect of the magnetic field on any amount of adsorbent catalyst with adsorbed first molecules, including all of the adsorbent catalyst, substantially all the adsorbent catalyst, some of the adsorbent catalyst, a few of the adsorbent catalyst, or one MSN nanoparticle having adsorbed first molecules. The adsorbent catalyst without adsorbed first molecules can be substantially equally affected by the applied magnetic field. The exposure to the magnetic field can be sufficient to move the catalyst towards the magnetic field. The exposure to the magnetic field can be sufficient to move the catalyst away from the magnetic field. The exposure can be sufficient to induce a magnetic field in each exposed catalyst particle. The exposure can be sufficient to cause the catalyst to move toward or away from a specific direction. The exposure can be sufficient to cause the catalyst to gather in a specific area. The remainder of the mixture can be transferred away from the first molecules, or the catalyst can be transferred away from the remaining mixture, such as by decanting, draining, centrifuging, siphoning, pumping, gravity, or a combination thereof.

Catalyst Including Mesoporous Silica Nanoparticles and a Catalytic Material.

In various embodiments, the present invention provides a catalyst. The catalyst includes a mesoporous silica nanoparticle. The catalyst can include a catalytic material including iron nanoparticles. The iron nanoparticles can be at least partially within the pores of the mesoporous silica nanoparticle. In some embodiments, the catalyst includes adsorbent groups thereon, as described herein. In other embodiments, the catalyst does not include adsorbent groups thereon.

The mesoporous silica nanoparticle is any suitable mesoporous silica nanoparticle, as is known to one of skill in the art. The mesoporous silica nanoparticle includes repeating —O—Si(R)$_2$— units, which form a silica matrix. The R group can independently designate any suitable substituent, including for example, siloxy, alkoxy, halo, or alkyl, wherein alkoxy or alkyl can be for example $C_1$-$C_{20}$ branched or straight chain. The repeating —O—Si(R)$_2$— units can be bound to any other suitable unit in the matrix. For example, an —O—Si(R)$_2$— unit can be bound directly to another silicon atom, forming an —O—Si(R)$_2$—O—Si(R)$_2$— unit. In another example, an —O—Si(R)$_2$— unit can be bound to an alkoxy group, which can in turn be bound to any suitable substituent, such as a silicon atom-containing substituent, such as another —O—Si(R)$_2$— unit, for example, to form —O—Si(R)$_2$—O-alkyl-O—Si(R)$_2$—.

As an initial step in the preparation of the catalyst, mesoporous silica nanoparticles (MSNs) can be prepared. MSNs and their preparation are described in, for example, U.S. Patent Application Publication Nos. 2006/0154069 (Lin et al.), 2006/0018966 (Lin et al.), and Linton et al., *Chem. Mater.* 2008, 20, 2878-2880. Any suitable procedure can be used to generate the mesoporous silica nanoparticle. In some examples, a mesoporous silica nanoparticle can be made by condensing an alkoxysilane. In some examples, the alkoxysilane can be tetramethylorthosilicate (TMOS), tetraethylortho silicate (TEOS), tetrakis(2-hydroxyethyl)orthosilicate (THEOS), methyldiethoxysilane (MDES), 3-(glycidoxypropyl)triethoxysilane (GPTMS), 3-(trimethyoxysilyl) propylacrylate (TMSPA), N-(3-triethoxysilylpropyl)pyrrole (TESPP), vinyltriethyoxysilane (VTES), methacryloxypropyltriethoxysilane (TESPM), diglycerylsilane (DGS), methyltriethoxysilane (MTMOS), trimethylmethoxysilane (TMMS), ethyltriethoxysilane (TEES), n-propyltriethoxysilane (TEPS), n-butyltriethyoxysilane (TEBS), 3-aminopropyltriethoxysilane (APTS), 2-(2,4-dinitrophenylamino)propyltriethoxysilane, mercaptopropyltriethoxysilane (TEPMS), 2-(3-aminoethylamino)propyltriethoxysilane, isocyanatopropyltriethoxysilane, hydroxyl-terminated polydimethylsiloxane, triethoxysilyl-terminated polydimethylsiloxane, methyltriethoxysilane (MTES), or triethoxysilyl-terminated poly(oxypropylene).

In some embodiments, acid or base treatment can allow hydrolysis of the alkoxysilane to give a reactive silanol, which can then react with other alkoxysilanes or silanols (e.g., to form —Si(R)$_2$—O—Si(R)$_2$— units) or with other reactive groups. In some embodiments, a reactive silanol can be provided by treatment of silica (e.g., $SiO_2$) with acid or base. Hydroxyl groups (e.g., R'—OH, wherein R' is any suitable substituent of suitable valancy, e.g., monovalent or divalent) from other compounds can condense with alkoxysilanes or silanols to give substituted silicones (e.g., —Si(R)$_2$—O—R'). Any suitable compound (e.g., silicon-containing or non-silicon containing) having any suitable number of hydroxyl or alkoxy groups (e.g., 1, 2, 3, 4, or more) can participate in the condensation, such that a wide variety of structures are possible for the mesoporous silica nanoparticle. For example, polyols can condense with multiple alkoxysilanes or silanols to give cross-linking of silicon atoms, e.g., HO—R'—OH can give —Si(R)$_2$—O—R'—O—Si(R)$_2$— units. Examples of suitable polyols can include any polyol that includes $C_{1-10}$ repeating alkylene oxide units, including polyols with more than one different $C_{1-10}$ repeating unit (e.g., ethylene oxide units such as in polyethylene glycol, propylene oxide units such as in propylene glycol, or a combination thereof such as in a co-polymer of ethylene and propylene glycol), wherein the polyol can have any suitable chain length or molecular weight. As conventionally prepared, MSNs are spherical, but they can also be prepared under conditions that yield other shapes such as rods.

The catalyst includes one or more catalytic materials in, on, or both in and on the mesoporous silica nanoparticle. The catalytic material can be on the outer surface of the nanoparticle. The catalytic material can be present inside none, some, or all of the pores of the mesoporous silica nanoparticle, and can be present or not present on the remainder of the surface of the mesoporous silica nanoparticle. The catalytic material can be evenly distributed within the pores of the mesoporous silica nanoparticle. The catalytic material can have any suitable form. In some examples, the catalytic material can include at least one of crystalline catalytic material, catalytic nanoparticles, a coating of catalytic material, and a coating of catalytic nanoparticles. In various embodiments, the catalyst can include any suitable amount of catalytic material, such as about 1-30 wt %, 1-20 wt %, or about 5-15 wt % catalytic material, or about 1 wt % or less, or about 2, 3, 3.5, 4, 4.5, 5, 5.5, 6, 6.5, 7, 7.5, 8, 9, 10, 12, 14, 16, 18, 20, 22, 24, 26, 28, or about 30 wt % of catalytic material or more. For example, the catalyst can include about 5-15 wt % Ni catalytic material, such as in the form of Ni or $Ni_2P$. For example, the catalyst can include about 1-30 wt %, 1-20 wt %, or about 5-15 wt % Fe catalytic material, such as in the form of Fe, $Fe_3O_4$, or $Fe_2O_3$.

The catalytic material can be any suitable type of catalyst. In some examples, the catalytic material can be at least one of nickel, nickel phosphide (e.g., $Ni_2P$), iron, iron oxide (e.g., $Fe_3O_4$ or $Fe_2O_3$), rhodium, ruthenium, gold, cobalt, cobalt oxide, palladium, platinum, and molybdenum. In some examples, the catalytic material is a hydrotreatment catalyst. The catalytic material can catalyze at least one of cracking, hydrogenation, reduction, decarboxylation, and hydrodeoxygenation. The catalyst can be any suitable hydrotreating catalyst. The hydrotreating catalyst can include one or more metals from IUPAC groups 6, 8, 9, and 10 of the periodic table of the elements. In some examples, the one or more metals can be selected from palladium (Pd), platinum (Pt), nickel (Ni), iron (Fe), and combinations thereof. In embodiments, the catalyst is a nickel-molybdenum (NiMo) catalyst including nickel and molybdenum. In some embodiments, the catalyst is a cobalt-molybdenum (CoMo) catalyst. In embodiments, $NiMo-Al_2O_3-SiO_2$ or $CoMo-Al_2O_3$ catalyst is utilized. In some embodiments, a Ni catalyst is utilized. In some embodiments, a molybdenum catalyst is utilized. In some embodiments, a catalyst with any suitable proportion of Ni and Mo is utilized.

In some examples, the mesoporous silica nanoparticle and the corresponding catalyst can be magnetic. Magnetism exhibited by the nanoparticle can be any kind of magnetism that allows the particle to be drawn in a particular direction by the effect of a magnetic field. The magnetism can include diamagnetism, paramagnetism, ferromagnetism, antiferromagnetism, ferrimagnetism, and superparamagnetism. The property of magnetism can result from iron oxide being included in or on the nanoparticle. The iron oxide can be any iron oxide known to one of skill in the art that can give magnetic properties to a nanoparticle, where in some embodiments the magnetic properties occur after further processing. Further processing can include reduction or oxidation of the iron oxide after inclusion in a nanoparticle. The iron oxide is at least one selected from $Fe_3O_4$ and $Fe_2O_3$.

The mesoporous silica nanoparticle can be transformed into a magnetic mesoporous nanoparticle via the addition of a magnetic iron oxide material. The iron oxide can be added by contacting the mesoporous silica nanoparticle with an iron precursor, optionally followed by a reduction or oxidation step. Thus, the catalyst can include a reaction product of a mesoporous silica nanoparticle and an iron precursor.

The mesoporous silica nanoparticle can be contacted with an iron precursor, followed by an optional reduction or oxidation step, to give a magnetic mesoporous nanoparticle. The iron precursor can be any suitable iron precursor. For example, the iron precursor can be $Fe(NO_3)_3$, including $Fe(NO_3)_3 \cdot 9H_2O$. Other examples include $(NH_4)_2Fe(SO_4)_2$, $NH_4Fe(SO_4)_2$, FeO, $Fe_3O_4$, $Fe_2O_3$, FeOCl, FeS, $Fe(OAc)_2$, $FeX_2$ or $FeX_3$ wherein X is independently chloro, bromo, or fluoro, $Fe_3(PO_4)_2$, $FeSO_4$, $FeTiO_3$, $Fe(NO_3)_3$, and the like, or any hydrate thereof. The reduction or oxidation is an optional step; in some embodiments, a reduction or oxidation is performed, while in other embodiments, a reduction or oxidation is not performed. The reduction or oxidation can be performed via any suitable means. In some examples, the reduction can be performed via application of $H_2$ gas. In some examples, the $H_2$ can be applied with heating.

In some embodiments, the mesoporous silica nanoparticle and the catalyst can have any suitable particle size, such as a particle size of approximately 50 nm-1200 nm, or about 300-600 nm, or about 50 nm or less, or about 100 nm, 150, 200, 250, 300, 325, 350, 375, 400, 425, 450, 475, 500, 525, 550, 575, 600, 650, 700, 750, 800, 850, 900, 950, 1000, 1050, 1100, 1150, or about 1200 nm or more. As used herein, "particle size" indicates the largest dimension of a particle, and corresponds to the diameter if the particle is approximately spherical. The iron catalytic nanoparticles can have any suitable particle size, such as about 0.01 nm-about 100 nm, 5 nm to about 15 nm, 8 nm to about 13 nm, or about 0.01 nm or less, or about 0.05, 0.1, 0.5, 1, 2, 3, 4, 5, 6, 7, 8, 9, 10, 11, 12, 13, 14, 15, 16, 17, 18, 19, 20, 25, 30, 40, 50, 75, or about 100 nm or more. In some embodiments, the iron nanoparticles have a particle size equal to or less than the pore size of the mesoporous silica nanoparticle. The mesoporous silica nanoparticle and the catalyst can have any suitable surface area, such as a surface area of approximately 100 $m^2/g$-1000 $m^2/g$, 200 $m^2/g$-500 $m^2/g$, or about 150 $m^2/g$-375 $m^2/g$, or about 100 $m^2/g$ or less, or about 150 $m^2/g$, 175, 200, 225, 250, 275, 300, 325, 350, 375, 400, 425, 450, 500, 600, 700, 800, 900, or about 1000 $m^2/g$ or more. The mesoporous silica nanoparticle and the catalyst can have any suitable pore size, such as a pore size of approximately 0.01 nm-100 nm, 1 nm-20 nm, about 5 nm-15 nm, or about 0.01 nm or less, or about 0.05 nm, 0.01, 0.1, 0.5, 1, 2, 3, 4, 5, 6, 7, 8, 9, 10, 11, 12, 13, 14, 15, 16, 17, 18, 19, 20, 25, 30, 40, 50, 75, or about 100 nm or more. In some examples, the average pore volume of the mesoporous silica nanoparticle and the catalyst can be any suitable pore volume, such as about 0.001 $cm^3/g$ to about 100 $cm^3/g$, 0.1 $cm^3/g$-6 $cm^3/g$, 0.25 $cm^3/g$-3 $cm^3/g$, about 0.5 $cm^3/g$-1.5 $cm^3/g$, or about 0.001 $cm^3/g$ or less, or about 0.005 $cm^3/g$, 0.01, 0.05, 0.1, 0.25, 0.5, 0.6, 0.7, 0.8, 0.9, 1, 1.1, 1.2, 1.3, 1.4, 1.5, 1.75, 2, 2.5, 3, 4, 5, 6, 10, 15, 20, 25, 50, 75, or about 100 $cm^3/g$ or more. In some embodiments, the pores are hexagonally arranged. In some examples, the silicon oxide matrix of the silica nanoparticle can have hexagonal symmetry.

In various embodiments, the catalyst can catalyze various hydrotreatment reactions such that they occur at a higher or lower rate with respect to one another. For example, the catalyst can catalyze any one of more of hydrogenation, reduction, decarboxylation, and hydrodeoxygenation at a higher or lower rate than any one or more of hydrogenation, reduction, decarboxylation, and hydrodeoxygenation. In some embodiments, in the presence of $H_2$, the catalyst can catalyst hydrocracking at a lower rate than the catalyst catalyzes at least one of hydrogenation, reduction, decarboxylation, and hydrodeoxygenation. In some embodiments, in the presence of $H_2$, the catalyst can catalyze hydrocracking of a fatty acid, such as a ($C_5$-$C_{50}$) fatty acid, at a lower rate than the catalyst catalyzes at least one of hydrogenation, reduction, decarboxylation, and hydrodeoxygenation of the fatty acid, such as at a temperature of about 200° C. to about 400° C. In some embodiments, in the presence of $H_2$, the catalyst can catalyze hydrocracking of a fatty acid, such as a ($C_5$-$C_{50}$) fatty acid, such that at about 100% conversion of the fatty acid, about 0.000,1 to about 30% of the yield of the reaction is hydrocracking product, or about 0.000,1% or less, or about 0.001, 0.01, 0.1, 1, 2, 3, 4, 5, 6, 7, 8, 9, 10, 11, 12, 13, 14, 15, 20, 25, or about 30% of the yield or more, such as at about 200° C. to about 400° C., or about 200° C. or less, or about 210° C., 220, 230, 240, 250, 260, 270, 280, 290, 300, 310, 320, 330, 340, 350, 360, 370, 380, 390, or about 400° C. or more. In various embodiments, the catalyst can catalyze hydrotreatment of a fatty acid, such as a ($C_5$-$C_{50}$) fatty acid, in the presence of $H_2$ such that about 100% conversion of the fatty acid occurs in about 1 h to about 20 h at a temperature of about 200° C. to about 400° C., or about 200° C. or less, or about 210° C., 220, 230, 240, 250, 260, 270, 280, 290, 300, 310, 320, 330, 340, 350, 360, 370, 380, 390, or about 400° C. or more. In some embodiments, the catalyst catalyzes at least one of hydrogenation, reduction, decarboxylation, and hydrodeoxygenation of at least one of a $C_{5-50}$ fatty acid $C_{1-50}$ ester and a triglyceride having $C_{5-50}$ fatty acid groups in the presence of $H_2$ at a temperature of about 200° C. to about 400° C.

Catalyst Including Mesoporous Silica Nanoparticles and a Catalytic Material, the Catalyst Having Adsorbent Groups Thereon.

Various embodiments of the present invention provide a catalyst that is or that includes an adsorbent catalyst, or a plurality of adsorbent catalysts. The adsorbent catalyst includes at least one adsorbent functional group bound to a mesoporous silica nanoparticle. Herein, any descriptions of the catalyst not specific to the function of the adsorbent groups can apply to a catalyst having adsorbent groups thereon, or to a catalyst not having adsorbent groups thereon. The adsorbent catalyst also includes at least one catalytic material, which can be at least one of on the outside of the mesoporous silica nanoparticle and within the pores of the mesoporous silica nanoparticle. The adsorbent functional material can adsorb particular molecules that can be catalyzed by the catalytic material.

In some examples, the adsorbent catalyst can catalyze particular reactions of certain materials at a higher or lower rate than a corresponding mesoporous nanoparticle including the catalytic material but not having the adsorbent functional groups bound thereto, or at a higher or lower rate than the catalytic material free of the mesoporous silica nanoparticle and without the proximate adsorbent functional groups. For example, in some embodiments, the adsorbent catalyst can catalyze the decarboxylation and hydrodeoxygenation of a fatty acid at a higher rate than a corresponding mesoporous nanoparticle including the catalytic material but not having the adsorbent functional group bound thereto. In some examples, the adsorbent catalyst can catalyze cracking of a fatty acid at a lower rate than a corresponding mesoporous nanoparticle including the catalytic material but not having the adsorbent functional group.

In some embodiments, the percent selectivity of the adsorbent catalyst toward catalyzation of cracking of a fatty acid is about 5-50%, 10-30%, or about 15-25% of the selectivity toward catalyzation of cracking of the fatty acid of a corresponding mesoporous nanoparticle including the catalytic material but not having the adsorbent functional group bound thereto. The percent selectivity of the adsorbent catalyst toward catalyzation of decarboxylation of a fatty acid can be about 50-600%, 200-400%, or about 250-350% of the selectivity toward catalyzation of decarboxylation of the fatty acid of a corresponding mesoporous nanoparticle including the catalytic material but not having the adsorbent functional group bound thereto. The percent selectivity of the adsorbent catalyst toward catalyzation of hydrodeoxygenation of a fatty acid can be about 50-1000%, 100-800%, 200-600%, 200-400%, or about 400-600% of the selectivity toward catalyzation of hydrodeoxygenation of the fatty acid of a corresponding mesoporous nanoparticle including the catalytic material but not having the adsorbent functional group bound thereto. In this paragraph, percent selectivity is defined such that if the percent selectivity of cracking, decarboxylation, and hydrodeoxygenation is added, the sum is 100%.

The adsorbent catalyst includes one or more adsorbent functional groups bound to the outer surface of a mesoporous silica nanoparticle. The adsorbent groups can be present inside none, some, or all of the pores of the nanoparticle, and can be present or not present on the remainder of the surface of the nanoparticle. Any suitable number and density of adsorbent functional groups can be on the mesoporous silica nanoparticle. For example, 0.001 mmol-1000 mmol, 0.01 mmol-50 mmol, or about 0.1 mmol-15 mmol of adsorbent functional groups can be on the nanoparticle per gram of the mesoporous silica nanoparticle.

The adsorbent functional group includes at least one selected from an amino($C_1$-$C_{20}$)alkyl group or a salt thereof, wherein the $C_1$-$C_{20}$ alkyl groups are independently optionally interrupted by one or two —NH— groups, a ($C_1$-$C_{20}$) alkyl carboxylic acid group or a salt thereof, a ($C_1$-$C_{20}$)alkyl sulfonic acid group or a salt thereof, and a perfluoro($C_1$-$C_{20}$)alkyl group, wherein the alkyl unit of the aminoalkyl group, the alkyl carboxylic acid group, the alkyl sulfonic acid group, and the perfluoroalkyl group is covalently bound to a mesoporous silica nanoparticle. The adsorbent functional group can include any suitable combination of aminoalkyl groups, alkyl carboxylic acid groups, the alkyl sulfonic acid groups, perfluoroalkyl groups, or salts thereof.

The adsorbent catalyst can include one or more amino ($C_1$-$C_{20}$)alkyl groups or salts thereof with alkyl units covalently bound to the mesoporous silica nanoparticle, wherein the $C_1$-$C_{20}$ alkyl groups are optionally interrupted by one or two —NH— groups. In some embodiments, the $C_1$-$C_{20}$ alkyl groups are not interrupted by one or two —NH— groups. The amino($C_1$-$C_{20}$)alkyl groups on a given nanoparticle can all have approximately the same length ($C_1$-$C_{20}$)alkyl group, or alternatively can have different lengths. Likewise, if an —NH— group interrupts an amino($C_1$-$C_{20}$)alkyl group, there can be the same number of —NH— groups interrupting each alkyl group, and there can be an —NH— group interrupting the alkyl group at the same location of the alkyl group, for all amino($C_1$-$C_{20}$)alkyl groups on a given nanoparticle. Also, —NH— groups can interrupt alkyl groups in varying numbers and location for all amino($C_1$-$C_{20}$)alkyl groups on a given nanoparticle. In one example, the adsorbent functional group can be an amino propyl group, wherein the propyl unit is covalently bound to the mesoporous silica nanoparticle, e.g., to an oxygen or silicon atom.

The adsorbent functional group can be one or more ($C_1$-$C_{20}$)alkyl carboxylic acid groups or salts thereof, with the ($C_1$-$C_{20}$)alkyl units covalently bound to the mesoporous silica nanoparticle. For example, the ($C_1$-$C_{20}$)alkyl carboxylic acid group can be —R—C(O)(OH), where R is ($C_1$-$C_{20}$)alkyl, or ($C_1$-$C_{10}$)alkyl, or ($C_2$-$C_6$)alkyl. The adsorbent functional group can be one or more ($C_1$-$C_{20}$)alkyl sulfonic acid group or salts thereof, with alkyl units covalently bound to the mesoporous silica nanoparticle. For example, the ($C_1$-$C_{20}$)alkyl sulfonic acid group can be —R—S(O)(O)(OH), where R is ($C_1$-$C_{20}$)alkyl, or ($C_1$-$C_{10}$)alkyl, or ($C_2$-$C_6$)alkyl. The adsorbent functional group can be one or more perfluoro($C_1$-$C_{20}$)alkyl groups, with the ($C_1$-$C_{20}$)alkyl units covalently bound to the mesoporous silica nanoparticle, such as perfluoro($C_1$-$C_{10}$)alkyl, or perfluoro($C_2$-$C_6$)alkyl. The ($C_1$-$C_{20}$)alkyl units on a given nanoparticle in a given type of adsorbent group can all have substantially the same length, or can have different lengths.

The salt of the aminoalkyl group, the alkyl carboxylic acid group, and the alkyl sulfonic acid group can be any suitable salt. The adsorbent groups on a given adsorbent catalyst can be substantially all be salts, can be substantially all not salts (e.g., can be free acids or amines), and any suitable combination thereof. The salt can include any suitable counterion. Examples of suitable negative counterions (e.g., for forming a salt with an amine, an ammonium salt) can include a halide, such as fluoride, chloride, bromide, or iodide. In other examples, the negative counterion can be a nitrate, hydrogen sulfate, dihydrogen phosphate, bicarbonate, nitrite, perchlorate, iodate, chlorate, bromate, chlorite, hypochlorite, hypobromite, cyanide, amide, cyanate, hydroxide, permanganate, an acid anion such as acetate or formate, or anions with negative charges greater than −1

(e.g., having in some embodiments one or more than one adsorbent functional group as counterion) such as oxide, sulfide, nitride, arsenate, phosphate, arsenite, hydrogen phosphate, sulfate, thio sulfate, sulfite, carbonate, chromate, dichromate, peroxide, or oxalate. Examples of suitable positive counterions (e.g., for forming a salt with a carboxylic acid or sulfonic acid) can include $Na^+$, $K^+$, $Cu^+$, $Li^+$, $Ag^+$, $Cs^+$, or anions with positive charges greater than 1 (e.g., for forming a salt with multiple acid groups) such as $Zn^{2+}$, $Fe^{2+}$, $Fe^{3+}$, $Ca^{2+}$, $Mg^{2+}$, $Zr^{2+}$, $Co^{2+}$, $Ni^{2+}$.

In some embodiments, the adsorbent catalyst can selectively adsorb one molecule or class of molecules over another molecule or class of molecules. For the adsorption to be selective, the selectivity can be less than exclusive. For example, if in a 1:1 mixture of compound or class of compounds A and compound or class of compounds B, an adsorbent catalyst adsorbs 48% A and 52% B, the adsorbent catalyst can be said to be selective toward adsorption of B. Also, if in a 1:1 mixture of A and B, an adsorbent catalyst adsorbs 25% A and 75% B, the adsorbent catalyst can be said to be selective toward adsorption of B. Also, if in a 1:1 mixture of A and B, an adsorbent catalyst adsorbs 1% A and 99% B, the adsorbent catalyst can be said to be selective toward adsorption of B. The adsorbent catalyst can selectively adsorb substantially all of the compound or class of compounds A and adsorb substantially none of the compound or class of compounds B. In any one of these examples of selectivity, one or more other compounds can be present, and similarly the adsorbent catalyst can be selective against adsorption of any one or more of the other compounds and selective towards adsorption of compound or class of compounds A or compound or class of compounds B. In various examples, the adsorbent catalyst can adsorb fatty acids at a higher rate than at least one of fatty acid esters and triglycerides.

EXAMPLES

The present invention can be better understood by reference to the following Examples which are offered by way of illustration. The present invention is not limited to the Examples given herein.

Example 1

Mesoporous Silica Nanoparticles Including Iron Nanoparticles

Materials.

Pluronic P104 was generously provided by BASF. Tetramethyl ortho silicate (TMOS), oleic acid, and Sylon (BSTFA (N,O-bis(trimethylsilyl)trifluoroacetamide) and TMCS (trimethylchlorosilane), 99:1) were purchased from Sigma Aldrich. Iron (III) Nitrate [Fe(NO$_3$)$_3$.9H$_2$O] was purchased from Fisher Scientific. All reagents were used as received without further purification.

Characterization.

Surface analysis of the catalyst was performed by nitrogen sorption isotherms in a Micromeritics Tristar analyzer. The surface areas were calculated by the Brunauer-Emmett-Teller (BET) method and the pore size distribution was calculated by the Barrett-Joyner-Halenda (BJH) method. The small angle powder X-ray diffraction (XRD) patterns were obtained with a Rigaku Ultima IV diffractometer using Cu target at 40 kV and 44 mA. Cu Kβ was removed using a monochromator. For transmission electron microscopy measurements, an aliquot of the powder was sonicated in methanol for 15 min. A single drop of this suspension was placed on a lacey carbon coated copper transmission electron microscope (TEM) grid and dried in air. The TEM examination was completed on a Tecnai G2 F20 electron microscope operated at 200 kV. Fourier transform infrared (FT-IR) spectra were recorded on Nicolet Nexus 470. Perkin Elmer ICP-MS was used to measure Ni loading and Agilent GC-MS was used to measure reaction products.

Catalytic Activity Measurements.

All catalytic reactions were performed in a batch reactor (Parr Instrument). In a typical experiment, the catalyst (10 mg) and oleic acid solution in hexanes (1 mM, 10 mL) were added in the reactor. The reactor was purged with $H_2$ at ambient temperature and was finally pressurized by $H_2$ to 30 bar. For kinetics study, the reaction was carried out at 290° C. for 1, 2, 3, 4, 5, and 6 h with constant stir rate. The reaction was allowed to cool to room temperature and the catalyst was separated. The reaction product was mixed with 1 mL Sylon (BSTFA (N,O-bis(trimethylsilyl)trifluoroacetamide) and TMCS (trimethylchlorosilane), 99:1) and heated to 70° C. for 2 h for further derivatization. The final mixture was analyzed by GC-MS. A similar experiment was conducted on hexane extract of *Nannochloropsis* sp.

Example 1.1

Catalyst Preparation

MSN was prepared using a nonionic block co-polymer Pluronic P104 surfactant. In a typical synthesis, P104 (7.0 g) was dissolved in aqueous HCl (273.0 g, 1.6 M). After stirring for 1 h at 56° C., tetramethylorthosilicate (TMOS, 10.64 g) was added and stirred for additional 24 h. The resulting mixture was further hydrothermally treated for 24 h at 150° C. in a high-pressure reactor. Upon cooling to room temperature, the white solid was collected by filtration, washed with copious amounts of methanol and dried in air. To remove the surfactant P104, the MSN material was heated at a ramp rate of 1.5° C. min$^{-1}$ and maintained at 550° C. for 6 h. MSN was then mixed with water and stirred at room temperature in order to rehydrate and regenerate the silanol groups, followed by filtration and drying. For impregnation, Fe(NO$_3$)$_3$.9H$_2$O (0.40 mmol, 0.16 g) was completely dissolved in water (0.48 mL). To this solution, the rehydrated MSN (0.4 g) was added and mixed. The solid mixture was calcined in air at a heating rate of 10° C. min$^{-1}$ to 300° C. and maintained at that temperature for 3 h followed by reduction at 400° C. for 6 hours in a constant flow of $H_2$ (1.67 mL/s).

Example 1.2

Properties of Fe-MSN

Figure 1B:
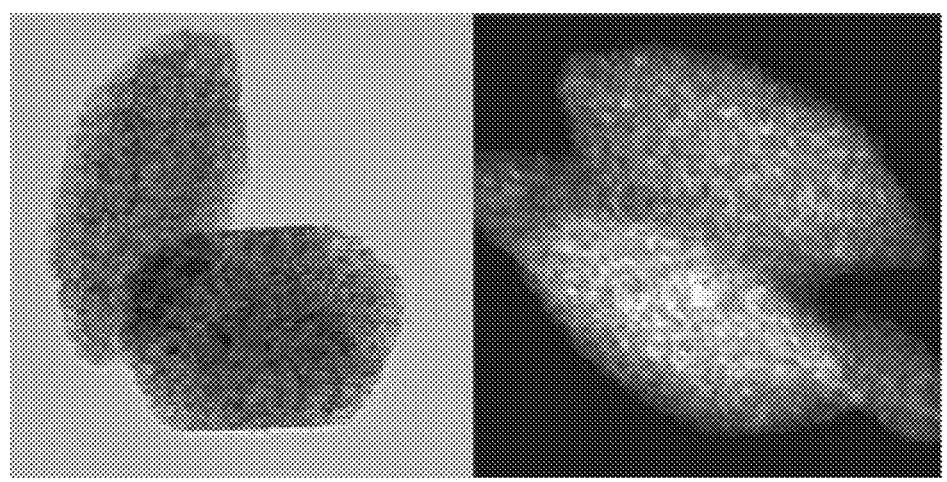
FIG. 1b illustrates transmission electron microscopy (left) and scanning transmission electron spectroscopy (right) images of Fe-MSN, in accordance with various embodiments.
Figure 1C:
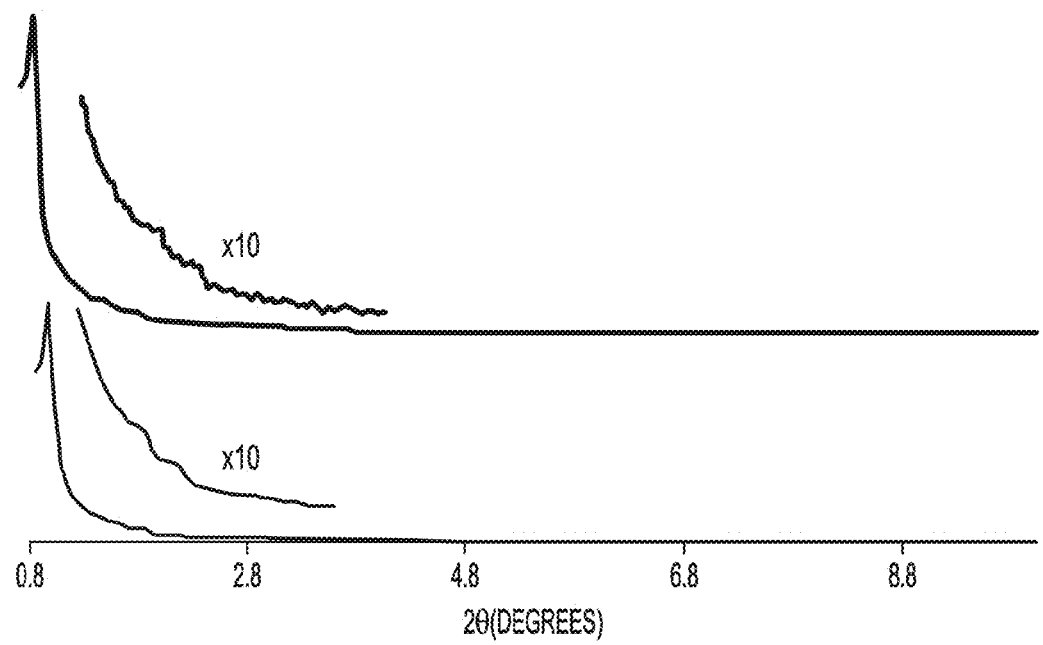
FIG. 1c illustrates XRD patterns of MSN (bottom) and Fe-MSN (top), in accordance with various embodiments.
Figure 1D:
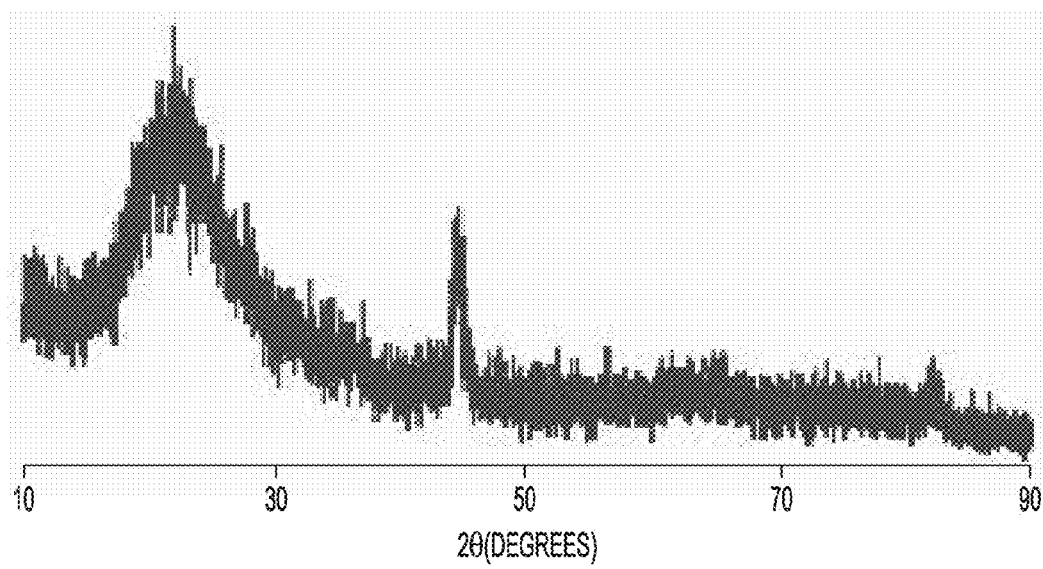
FIG. 1d illustrates a wide angle XRD pattern of Fe-MSN, in accordance with various embodiments.

The textural properties of MSN support and Fe-MSN catalyst are summarized in Table 1. Inductively coupled plasma (ICP) measurement indicated 6.0 wt % Fe was immobilized on the MSN support. Formation of the Fe nanoparticles led to approximately 10% decrease in the surface area and pore volume of the support; however, its nitrogen sorption isotherm remained type IV, confirming retention of the mesoporous character (FIG. 1a, showing MSN (open circles) and Fe-MSN (filled circles)). TEM and scanning transmission electron microscopy (STEM) imaging suggested that the Fe nanoparticles were located mainly inside the pores of the MSN (FIG. 1b). Low angle XRD analysis confirmed that the structure of the support was not affected by the formation of Fe nanoparticles, as it preserved the p6 mm pattern typical of SBA-15 type materials (FIG. 1c, showing MSN (bottom) and Fe-MSN (top), with insets showing 10× magnified 110 and 200 reflections). Wide-angle XRD showed a pattern of peaks corresponding to the body centered cubic phase of crystalline iron nanoparticles (FIG. 1d). The relatively wide reflections indicated small crystallite size of the iron nanoparticles, estimation using the Scherrer equation indicated their size was on the same order as the width of the mesopores, which suggested nanoparticle growth was restricted by the size of the pores.

TABLE 1

Textural properties of the support and catalyst.

|  | MSN | Fe-MSN |
| --- | --- | --- |
| Surface area ($m^2g^{-1}$) | 331 | 295 |
| Pore volume ($cm^3g^{-1}$) | 0.97 | 0.88 |
| Pore diameter (nm) | 11.1 | 10.9 |

Example 1.3

Oleic Acid Hydrotreatment with Fe-MSN

Figure 2A:
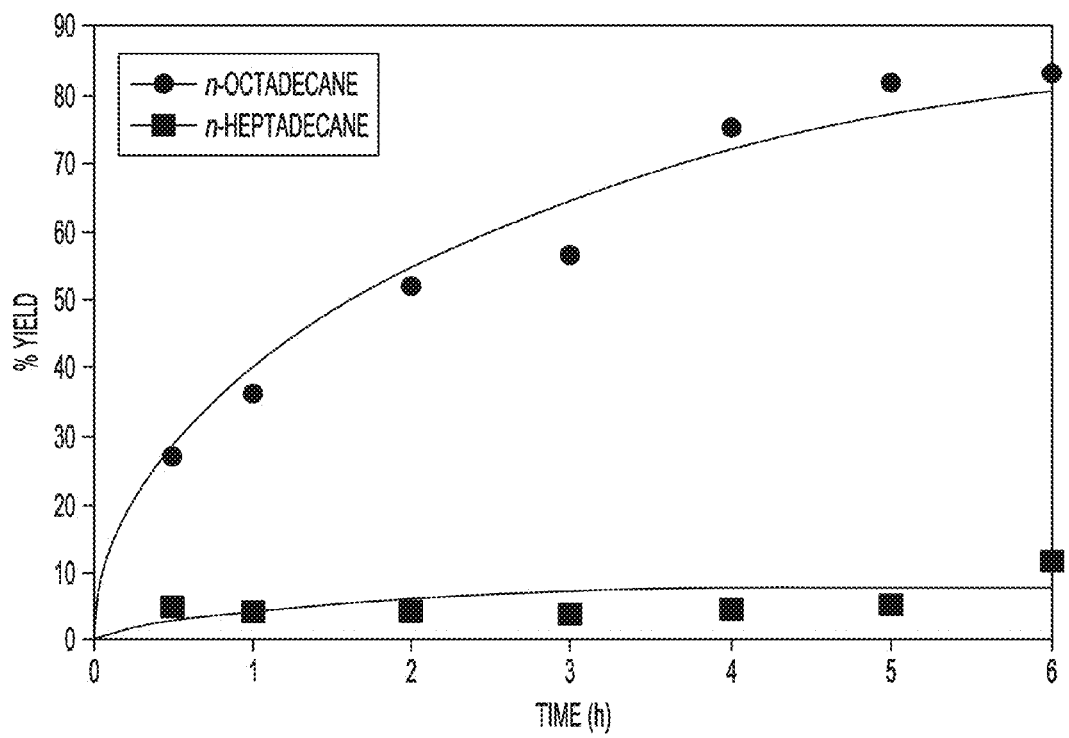
FIG. 2(a) illustrates the yield of hydrocarbon products versus time for oleic acid hydrotreatment catalyzed by Fe-MSN, in accordance with various embodiments.
Figure 2B:
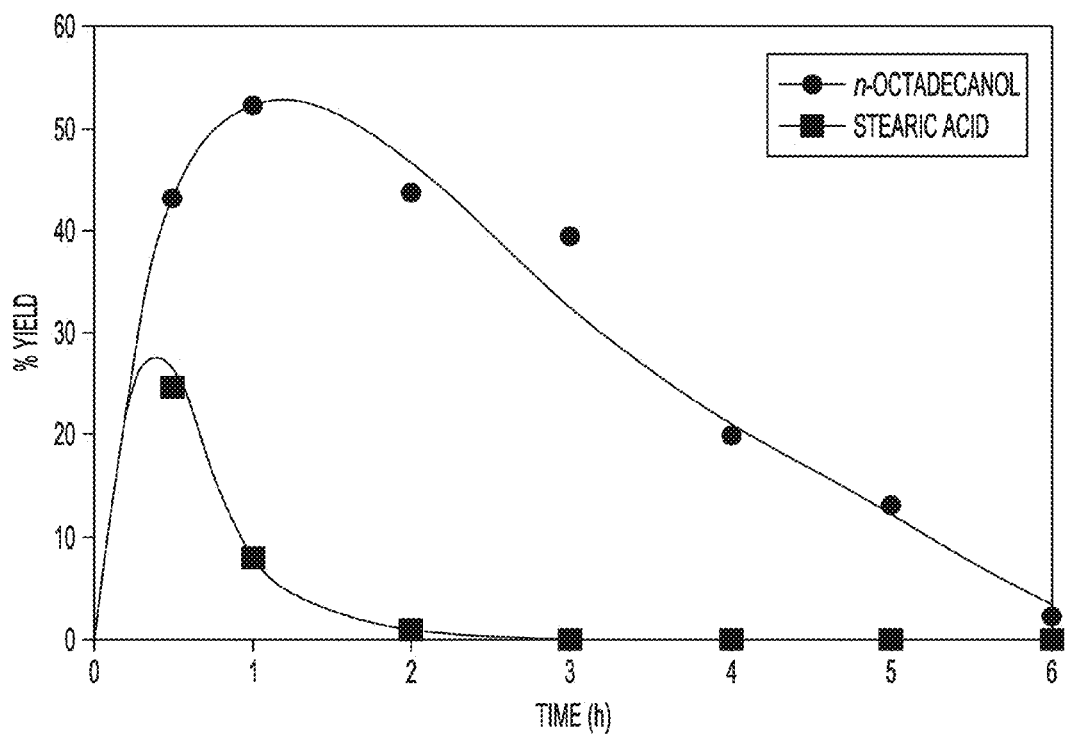
FIG. 2(b) illustrates the yield of intermediate materials versus time for oleic acid hydrotreatment catalyzed by Fe-MSN, in accordance with various embodiments.

The kinetics of the hydrotreatment of oleic acid (1 mM, 10 mL) with Fe-MSN (10 mg) at 290° C. and 30 bar $H_2$ pressure are shown in FIGS. 2a-b, with FIG. 2a showing hydrocarbon products at various times, and FIG. 2b showing reaction intermediates at various times. No oleic acid was detected after 0.5 h and the mayor hydrocarbon product obtained after 6 h was n-octadecane, indicating hydrodeoxygenation was the major reaction route. The yield of n-octadecane ($C_{18}$) increased continuously to 83% in 6 h, while that of n-heptadecane ($C_{17}$) grew slowly to 12% after 6 h (FIG. 2a). In sharp contrast to the hydrogenation of oleic acid using nickel supported on MSN under the same reaction conditions (72% hydrocracking, 25% $C_{17}$ and 3% $C_{18}$), the hydrocracking was almost eliminated with Fe-MSN catalyst as it was only observed after 6 h reaction (3% yield).

Figure 3:
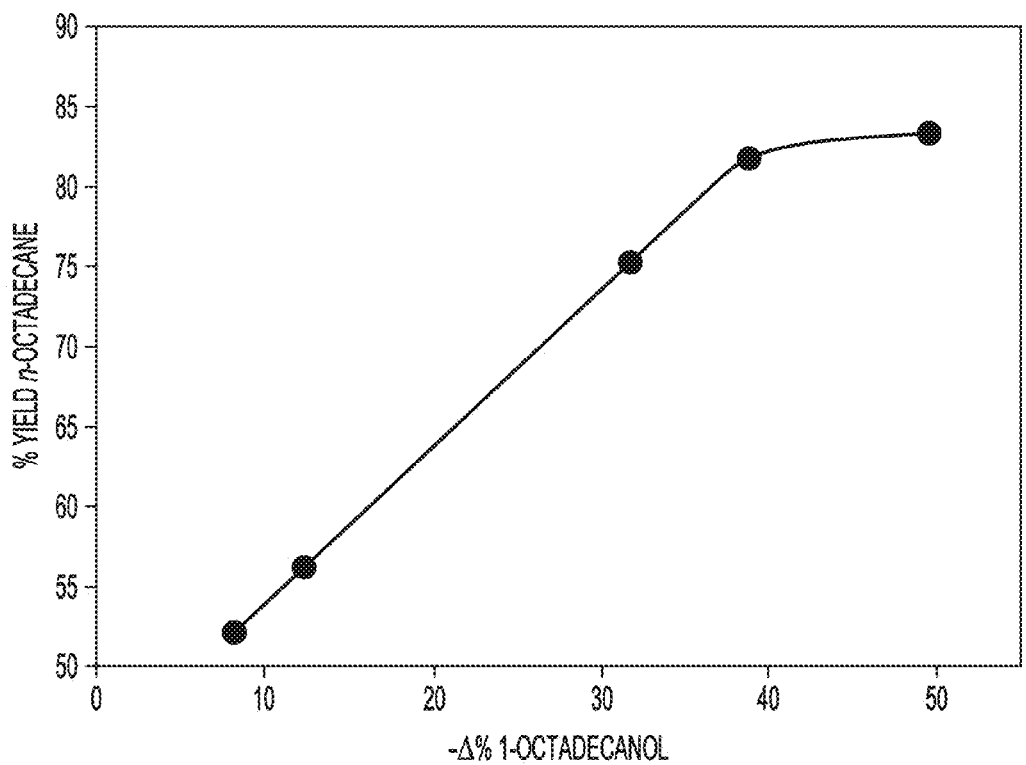
FIG. 3 illustrates the yield of n-octadecane versus the decrease in yield of 1-octadecanol for oleic acid hydrotreatment catalyzed by Fe-MSN, in accordance with various embodiments.

Stearic acid and 1-octanol were observed with highest yields at early reaction times, peaking before 0.5 and 2 h respectively and then decreasing, which suggested that both species are reaction intermediates (FIG. 2b). Since stearic acid disappeared earlier than octadecanol, and octadecenol was not observed, the reaction may have proceeded initially by a fast hydrogenation of C=C, followed by reduction of the COOH group to alcohol, which eventually underwent hydrodeoxygenation to give the major reaction product. The yield of n-octadecane increased linearly with the decrease in 1-octadecanol until 5 h, supporting the idea that the alcohol is an intermediate in the hydrodeoxygenation pathway (FIG. 3, showing production of n-octadecane as a function of the decrease in yield of 1-octadecanol). After 5 h the production of n-octadecane plateaued, suggesting the system reached equilibrium.

Figure 4:
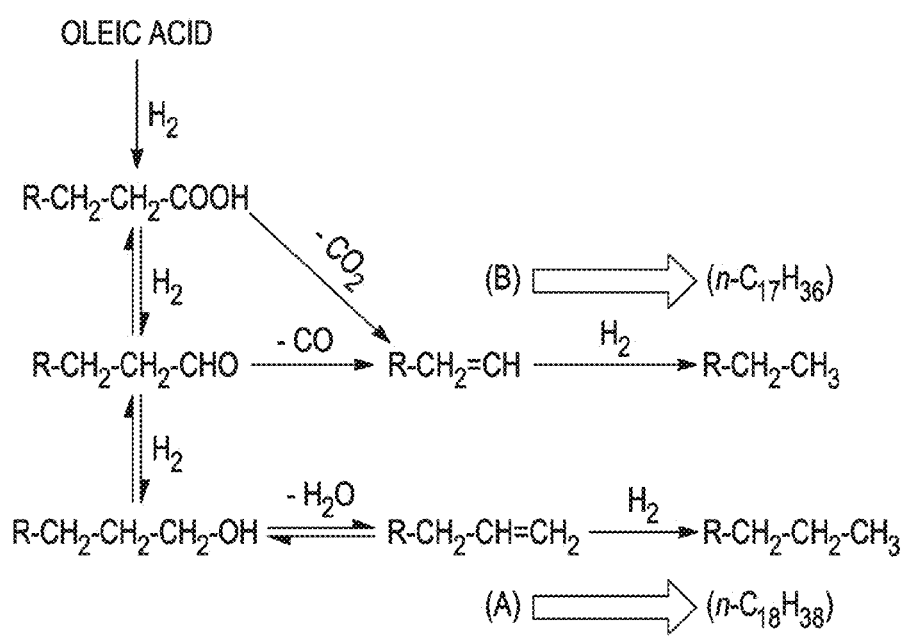
FIG. 4 illustrates mechanisms for conversion of oleic acid into n-octadecane (pathway a) and n-heptadecane (pathway b) from the intermediates 1-octadecanol and octadecanal, respectively, with R=n-pentadecyl, in accordance with various embodiments.

The formation of n-octadecane from 1-octadecanol could take place as a two-step process, first involving dehydration of 1-octadecanol to give 1-octadecene, which would then be hydrogenated to the saturated product (FIG. 4, pathway a, R=n-pentadecyl). n-Heptadecane could form either by direct decarboxylation of stearic acid or by decarbonylation of octadecanal, which could also be an intermediate in the formation of 1-octadecanol (FIG. 4, pathway b). However, neither octadecanal nor octadecene were detected in these experiments, therefore their hypothetical participation in the reaction would likely only occur if they are short lived under the conditions employed.

The quick conversion of oleic acid to stearic acid suggests the hydrogenation of double bonds can be very fast under the reaction conditions. Since suspensions of iron nanoparticles can catalyze alkene hydrogenation at room temperature and pressures of, for example, 1 bar $H_2$, if octadecene and heptadecene form as intermediates they are most likely transformed at a high rate into octadecane and heptadecane, respectively. Indeed, performing the Fe-MSN catalyzed hydrogenation of oleic acid under milder conditions allowed the detection of 1-heptadecene and 1-octadecene (about 2% yields at 10 bar $H_2$ and 270° C.).

Since Fe-catalyzed reduction of acetic acid to acetaldehyde can occur at 1 bar $H_2$ in the range of 250-350° C., it was expected that Fe-MSN would catalyze the hydrogenation of stearic acid to octadecanal under the conditions employed in the present Example. However, the equilibrium constant for the hydrogenation of octadecanal to 1-octadecanol at 260° C. is approximately 30, which can explain why the aldehyde is scarce under the reaction conditions of the present Example. A small amount of octadecanal could only be observed when performing the reaction at a lower temperature (2.4% yield at 30 bar $H_2$ and 230° C.). Since no aldehyde could be detected at temperatures 250° C. or higher, the apparent activation energy for the reduction to alcohol over Fe-MSN is likely easily overcome under the conditions of the present Example. Thus, if under the reaction conditions of the present Example the rate of interconversion between the aldehyde and alcohol is fast, the ratio of n-heptadecane to n-octadecane products in the overall reaction can be controlled by the relative rates of aldehyde decarbonylation and alcohol dehydration. Fe-MSN may favor the latter reaction, since iron oxides can catalyze the dehydration of ethanol at temperatures above 200° C.

Figure 5A:
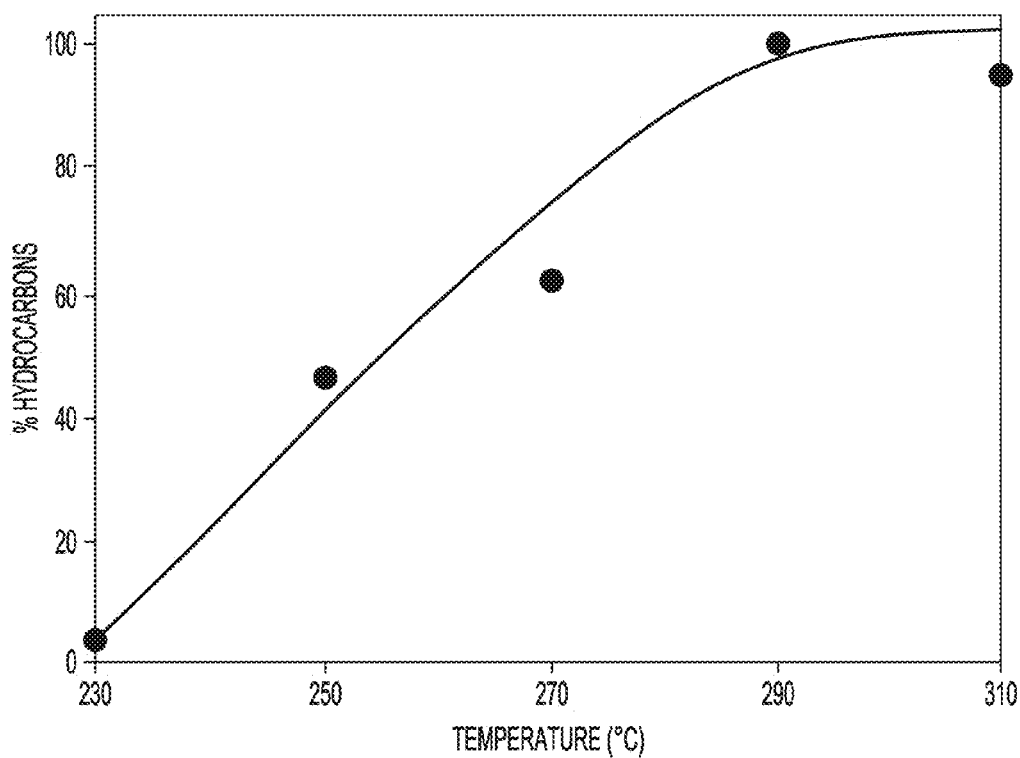
FIG. 5a illustrates the effect of temperature on the yield of hydrocarbons in an Fe-MSN catalyzed hydrotreatment of oleic acid, in accordance with various embodiments.
Figure 5B:
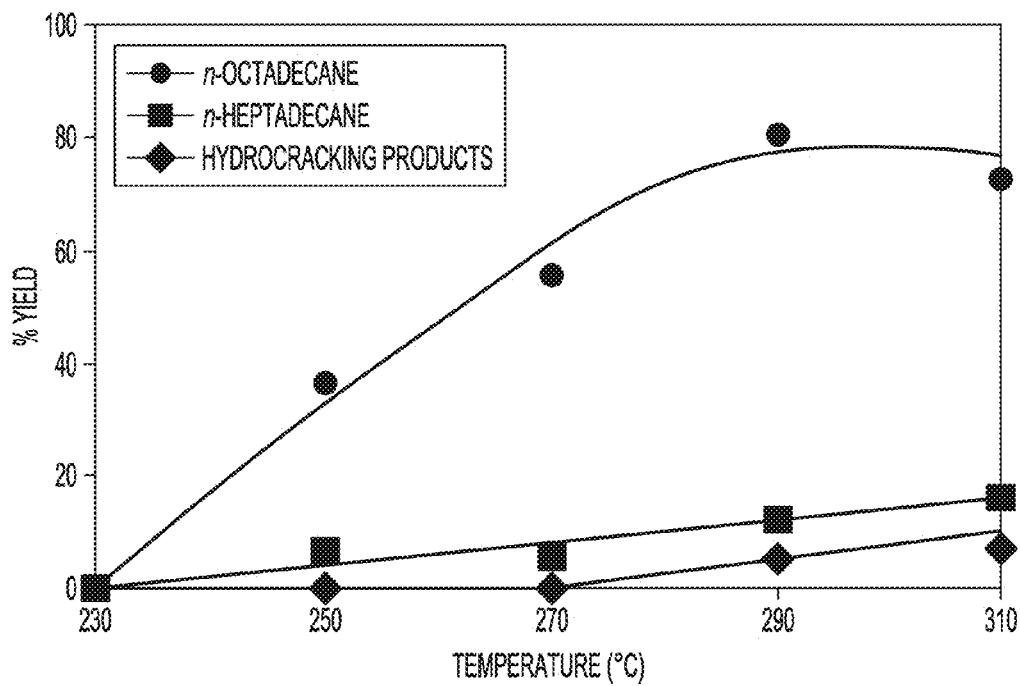
FIG. 5b illustrates the effect of temperature on the distribution of hydrocarbons in an Fe-MSN catalyzed hydrotreatment of oleic acid, in accordance with various embodiments.

FIGS. 5a-b show data at 6 h of reaction of the Fe-MSN catalyst with oleic acid at 30 bar $H_2$. The production of liquid hydrocarbons was very low at 230° C. but increased dramatically with temperature to almost 100% at 290° C. (FIG. 5a). Analysis of hydrocarbon distribution (FIG. 5b) revealed that the increase in yield was mainly due to n-octadecane (from under 1% at 230° C. to 83% at 290° C.). While the yield of n-hepadecane also increased with temperature, the effect was lower (from under 1% at 230° C. to 16% at 310° C.). The products of hydrocracking were not observed at 230° C. but were detected only at temperatures higher than 250° C. The increase in hydrocracking with temperature was even lower than that of n-heptadecane (from 1% at 250° C. to 7% at 310° C.). These observations suggest that the apparent activation energies of the key steps that lead to the three products have the relative order $E_{a\ alcohol\ dehydration} < E_{a\ decarbonylation} < E_{a\ cracking}$ when using Fe-MSN as a catalyst.

Figure 6A:
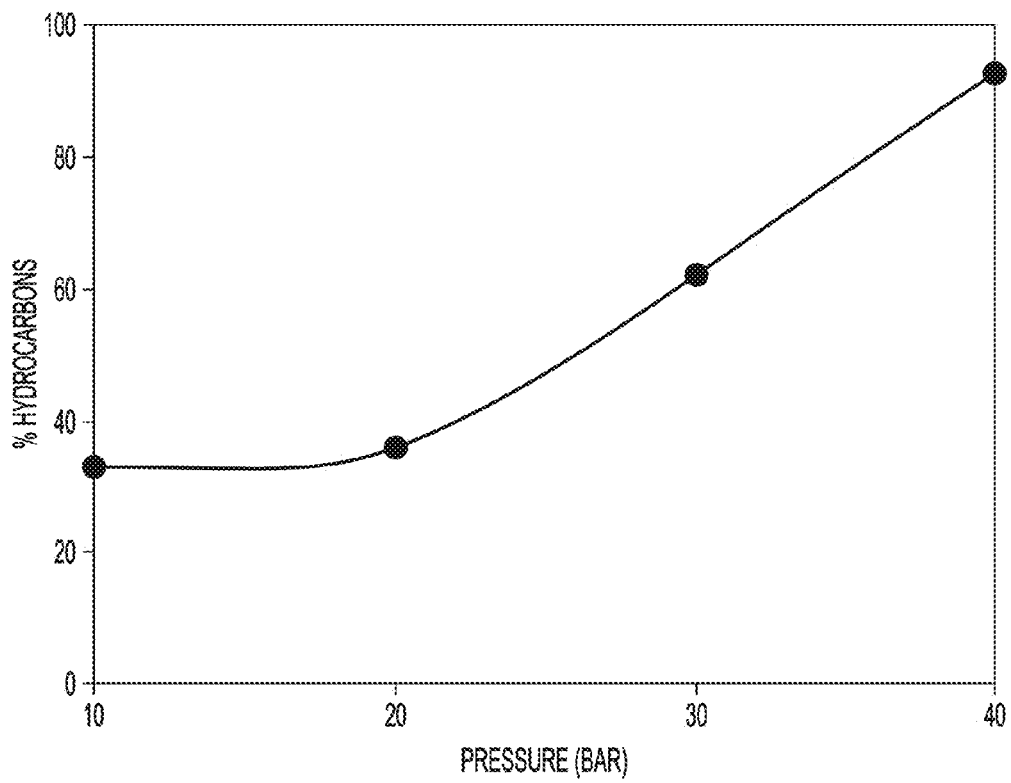
FIG. 6a illustrates the effect of $H_2$ pressure on the yield of hydrocarbons in an Fe-MSN catalyzed hydrotreatment of oleic acid, in accordance with various embodiments.
Figure 6B:
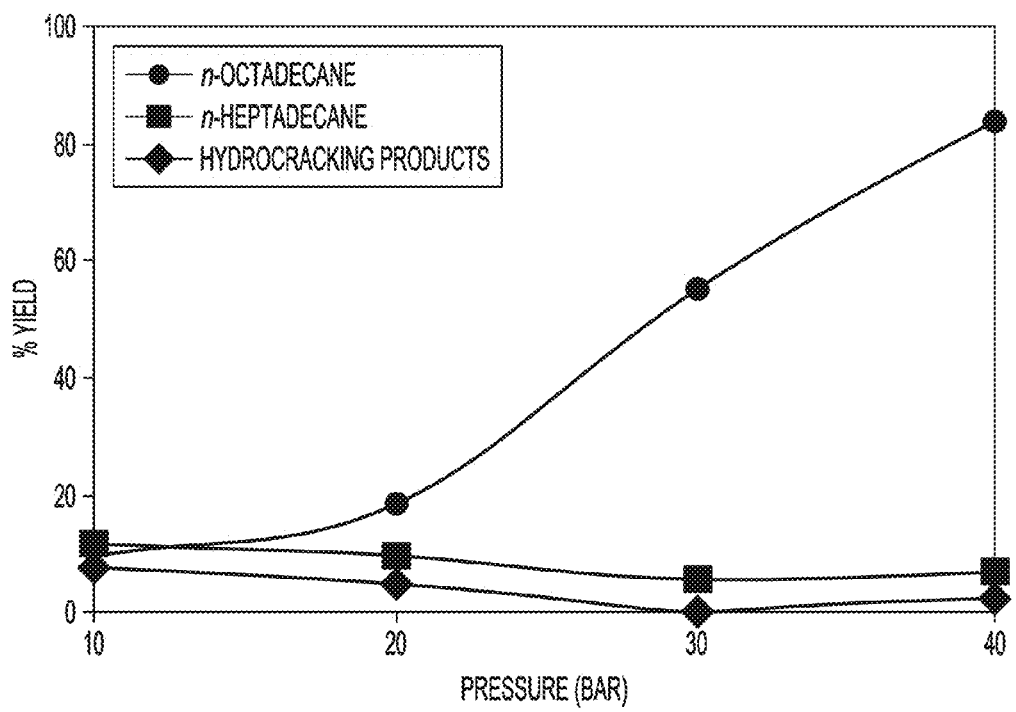
FIG. 6b illustrates the effect of $H_2$ pressure on the distribution of hydrocarbons in an Fe-MSN catalyzed hydrotreatment of oleic acid, in accordance with various embodiments.

FIGS. 6a-b show data at 6 h of reaction of the Fe-MSN catalyst with oleic acid at 270° C. The conversion of oleic acid was proportional to the pressure of hydrogen applied (FIG. 6a). However, at 270° C. the total hydrocarbon yield showed little sensitivity to an increase in pressure from 10 to 20 bar, going only from 33% to 36% and approached full conversion at higher pressures (FIG. 6a). Low hydrogen pressures increased the selectivity for decarbonylation and hydrocracking, and high pressures favored the hydrodeoxygenation product n-octadecane (FIG. 6b). This dependence of selectivity on hydrogen pressure may have been a result of participation of $H_2$ in the equilibrium between octadecanal and 1-octadecanol, the branching step in the process. As hydrogen is used to convert the octadecanal into 1-octadecanol, increasing the amount of the gas shifts the equilibrium towards the alcohol, favoring the route to n-octadecane, while decreasing the amount of the gas has the opposite effect leading to the n-heptadecane pathway.

Example 1.4

Hypothetical Mechanism of Carboxylic Acid Reduction with Fe-MSN

Figure 7:
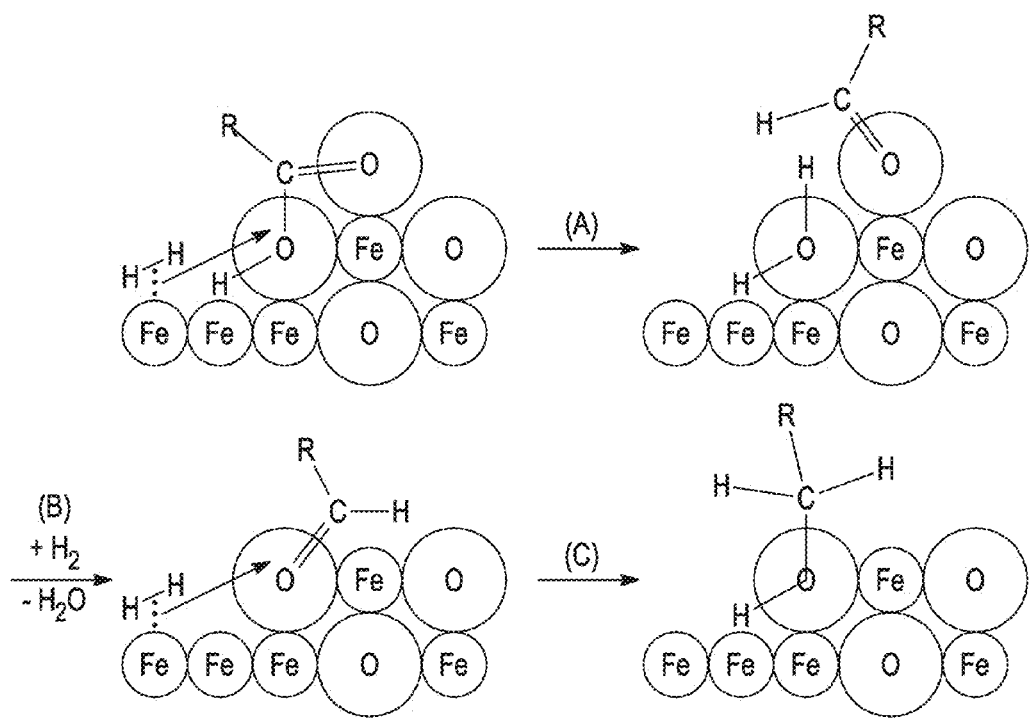
FIG. 7 illustrates a hypothetical mechanism for reduction of carboxylic acid groups on the surface of the partially oxidized Fe nanoparticles of Fe-MSN, in accordance with various embodiments.

Embodiments of the present invention are not restricted to any specific mechanism of operation. It is hypothesized that H2 is first bound at a Fe(0) phase and then reduces an adjacent acid bound at an iron oxide phase. The XRD analysis of the catalyst in Example 1 showed only metallic iron, and gave no evidence of oxide (FIG. 1d). However, given its low redox potential, oxidation of iron nanoparticles is a fast process, in which sub-nanometer layers of oxide form upon exposure to air for less than one minute. XPS analysis of an embodiment revealed the presence of the oxide in the catalyst, which suggested that the amount of iron oxide is small and/or it is not crystalline. In addition, the emergence of a weak reflection at 35° in the XRD pattern of an embodiment of the spent catalyst also suggested the formation of iron oxide during the reaction. Thus, the process appeared to involve an active transformation of the surface of the catalyst as it is reduced by the $H_2$ and oxidized by the carboxylic acid, through a reverse Mars-Van Krevelen mechanism (FIG. 7, showing (a) reduction to aldehyde, and (c) further reduction to alcohol).

Figure 8:
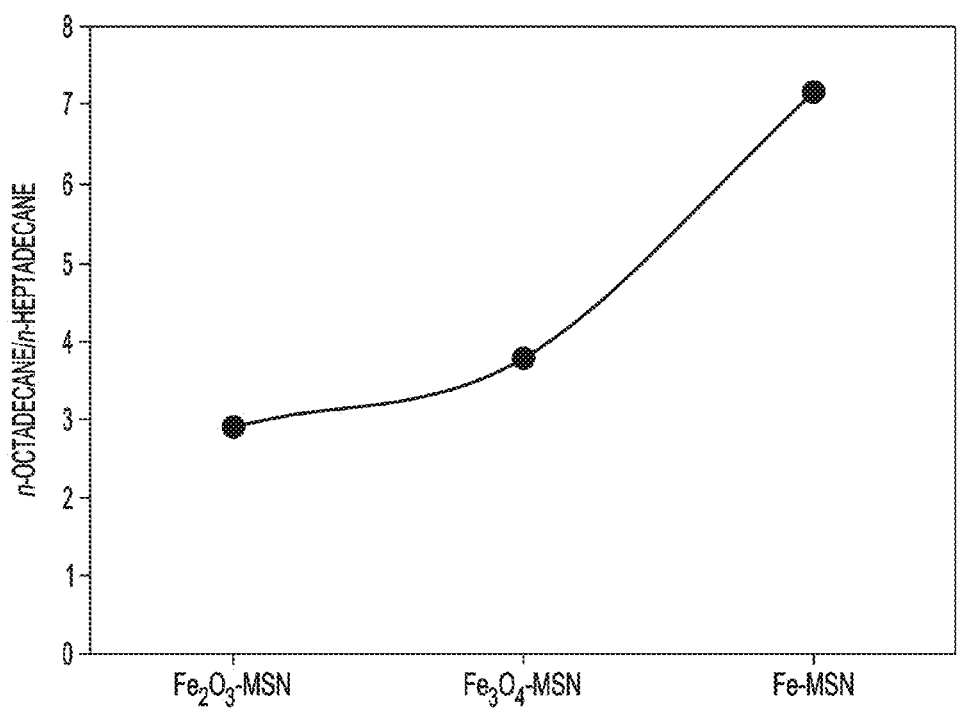
FIG. 8 illustrates product selectivity as a function of the oxidation state of the Fe in the Fe-MSN catalyst, in accordance with various embodiments.

By controlling the reduction temperature of the parent iron-impregnated MSN, two other materials were prepared with different phases of iron: $Fe_2O_3$-MSN and $Fe_3O_4$-MSN, as determined by their XRD patterns. Consistent with the hypothetical mechanism, the $C_{18}$: $C_{17}$ selectivity of the reaction was proportional to the degree of reduction of the iron in the catalysts (FIG. 8). The more oxidized $Fe_2O_3$-MSN gave the lowest yield of n-octadecanol, suggesting that the reduction of a significant fraction of oleic acid stopped at the carbonyl stage, leading the way to the decarbonylation product n-heptadecane. On the other hand, the reduced Fe-MSN led to a higher selectivity for n-octadecane, which results from the formation of 1-octadecanol.

The difference in selectivity for n-octadecane between Fe-MSN and Ni-MSN (83% versus 3% at 290° C. and 30 bar $H_2$) can be due to differences between the strengths of the metal-oxygen bonds in the catalysts. The stronger Fe—O bonds would lead to longer residence times of the oleic acid as it binds through its oxygen atoms at the vacancies of the iron oxide surface (FIG. 7), leading to a complete reduction to alcohol rather than the partial reduction to aldehyde that would occur if the carboxylic groups bound more weakly to the surface of the catalyst.

Example 1.5

Conversion of Microalgae Oil into Green Diesel

Figure 9:
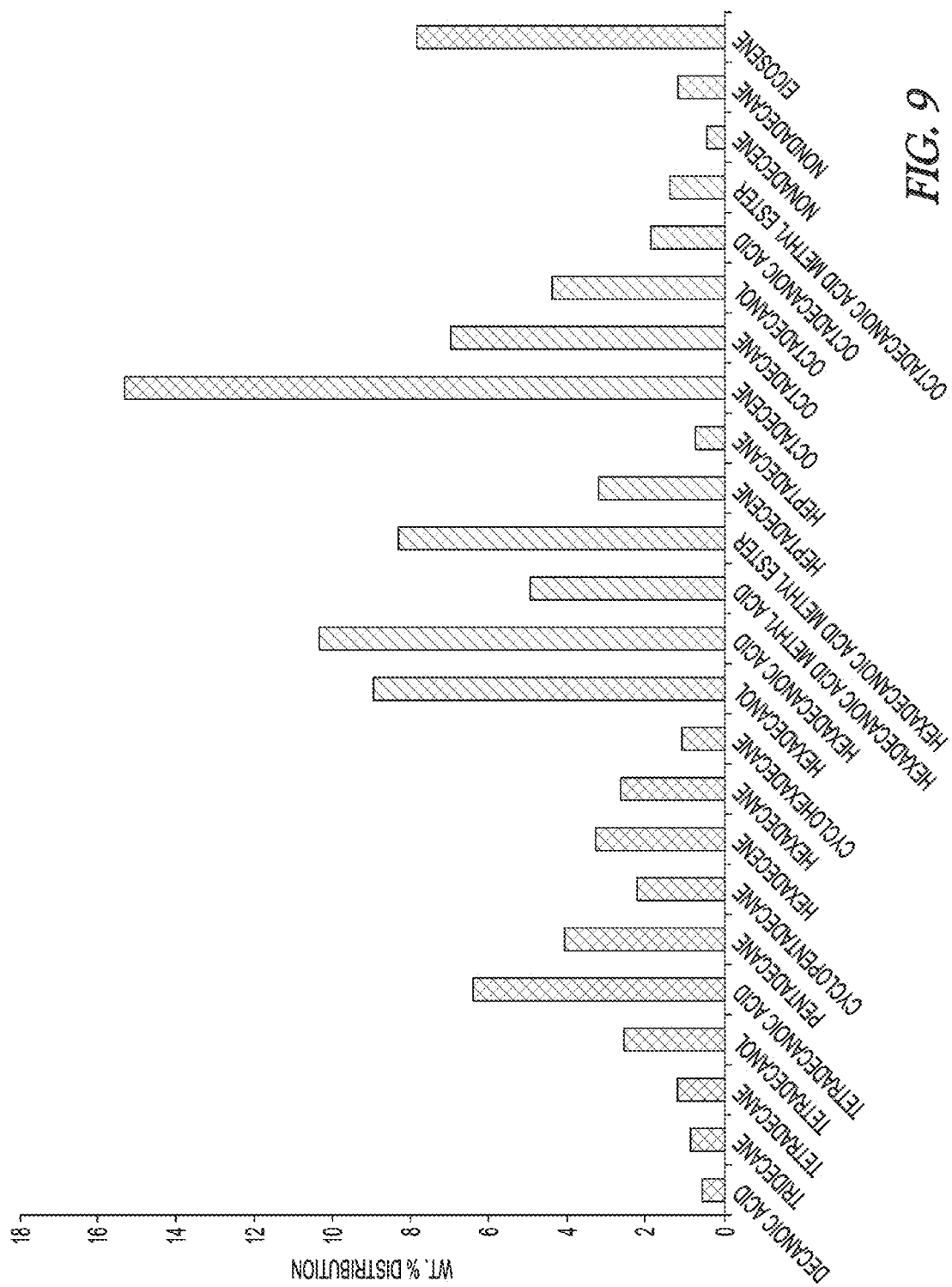
FIG. 9 illustrates the distribution of liquid products of Fe-MSN catalyzed hydrotreatment of *Nannochloropsis* sp. extract, in accordance with various embodiments.

The lipids from *Nannochloropsis* sp. microalgae were extracted with hexanes. The crude microalgal extract was directly hydrotreated with 10 mg of the Fe-MSN catalyst at 290° C. under 30 bar $H_2$ for 6 h in batch mode. GC-MS analysis showed the extract contained various liquid hydrocarbons (FIG. 9). It was found that 19 wt % of the product were saturated FFAs, and 33 wt % of the FFA in the original extract were unsaturated. Similarly, the high ratio of octadecane:heptadecane (10:1) obtained during the hydrotreatment of microalgal extract is consistent with our observation that the Fe-MSN favors hydrodeoxygenation rather than decarbonylation.

Surprisingly, octadecene (15.3 wt %) was the major hydrocarbon product. The fatty acid composition of the crude microalgae extract was analyzed in GC-MS and was found to include: saturated $C_{14}$ fatty acids (11.1%), saturated $C_{16}$ fatty acids (49.6%), unsaturated $C_{16}$ fatty acids (29.6%), saturated $C_{18}$ fatty acids (1.3%), unsaturated $C_{18}$ fatty acids (3.3%), along with smaller amounts of $C_{12}$, $C_{15}$, $C_{17}$ and $C_{20}$ fatty acids (5.15 wt % total). However, the higher yield of $C_{18}$ hydrocarbons after hydrotreatment of crude microalgae extract evidences that Fe-MSN can hydrogenolyse and subsequently hydrodeoxygenate neutral lipids like di- and triglyceride to alkanes. This influences the hydrogen consumption and therefore the product yield and distribution. The presence of octadecene after hydrotreatment of crude microalgae extract is consistent with the observation of unsaturated hydrocarbons at low $H_2$ pressure (FIG. 7b), as the availability of $H_2$ is diminished by its consumption in the hydrodeoxygenation and hydrogenolyses.

Example 2

Adsorbent Functional Groups

General.

Pluronic was provided by BASF. Tetramethyl orthosilicate (TMOS) was purchased from Sigma Aldrich. 3-Aminopropyl trimethoxysilane (APTMS) was purchased from Gelest. Nickel nitrate hexahydrate [$Ni(NO_3)_2 \cdot 6H_2O$] and ammonium phosphate [$(NH_4)_2HPO_4$] were purchased from Fisher Scientific.

Example 2.1

Synthesis of Mesoporous Silica Nanoparticles (MSN)

The nonionic surfactant Pluronic P104 (7.0 g) was added to HCl (273.0 g, 1.6 M). After stirring for 1 h at 56° C., tetramethylorthosilicate (TMOS, 10.64 g) was added and stirred for an additional 24 h. The resulting mixture was further post hydrothermally treated for 24 h at 150° C. in a high-pressure reactor. Upon cooling to room temperature, the white solid was collected by filtration, washed with copious amounts of methanol and dried in air. To remove the surfactant P104 by calcination, the MSN material was heated at a ramp rate of 1.5° C. $min^{-1}$ and maintained at 550° C. for 6 h.

Example 2.2

Synthesis of Nickel Nanoparticles in the Pores of MSN (Ni-MSN)

MSN was mixed with water and stirred at room temperature in order to rehydrate and regenerate the silanol groups, followed by filtration and drying. $Ni(NO_3)_2 \cdot 6H_2O$ (0.55 mmol, 0.16 g) was completely dissolved in water (0.48 mL). To this solution, the rehydrated MSN (0.4 g) was added and mixed. The solid mixture was calcined in air at a heating rate of 2° C. $min^{-1}$ to 500° C. and maintained at that temperature for 6 h followed by reduction at 450° C. for 5 hours in a constant flow of $H_2$ (0.5 mL/s).

Example 2.3

Synthesis of Nickel Phosphide Nanoparticles in the Pores of MSN Ni$_2$P-MSN)

Ni(NO$_3$)$_2$.6H$_2$O (0.55 mmol, 0.16 g) and (NH$_4$)$_2$HPO$_4$ were completely dissolved in water (0.48 mL). To this solution, the rehydrated MSN (0.4 g) was added and mixed. The solid mixture was calcined in air at a heating rate of 2° C. min$^{-1}$ to 500° C. and maintained at that temperature for 6 h followed by temperature programmed reduction (TPR) at 650° C.

Example 2.4

Synthesis of 3-Aminopropyl Trimethoxysilane Functionalized Ni-MSN (AP-Ni-MSN)

Amine functionalized materials were prepared by grafting APTMS (0.5 mmol, 0.09 g for AP-Ni-MSN-0.5 and 2 mmol, 0.36 g for AP-Ni-MSN-2) to the surface of Ni-MSN (1 g) in refluxing toluene (100 mL) for 24 hours. The resulting solid was filtered, washed with methanol and dried under vacuum for 24 h.

Example 2.5

Characterization

Surface analysis of the catalyst was performed by nitrogen sorption isotherms in a Micromeritics Tristar surface area and porosity analyzer. The surface areas were calculated by the Brunauer-Emmett-Teller (BET) method and the pore size distribution was calculated by the Barrett-Joyner-Halenda (BJH) method. The small angle powder X-ray diffraction patterns were obtained with a Rigaku Ultima IV diffractometer using Cu target at 40 kV and 44 mA. Cu Kβ was removed using a monochromator. For transmission electron microscopy measurements, an aliquot of the powder was sonicated in methanol for 15 min. A single drop of this suspension was placed on a lacey carbon coated copper TEM grid and dried in air. The TEM examination was completed on a Tecnai G2 F20 electron microscope operated at 200 kV. Fourier transform infrared (FT-IR) spectra were recorded on Nicolet Nexus 470. TPD measurements were performed in Autochem. Perkin Elmer ICP-MS was used to measure Ni loading and Agilent GC-MS was used to measure reaction products.

Example 2.6

General Procedure for One-Step Batch Reaction, Also Called Simultaneous Catalysis or Tandem Sequestration Catalysis All catalytic reactions were performed in a batch reactor (Parr Instrument). In a typical experiment, the catalyst (10 mg) and oleic acid solution in hexanes (1 mM, 10 mL) were added in the reactor. The reactor was purged with H$_2$ at ambient temperature and was finally pressurized by H$_2$ to 30 bar. The reaction was carried out at 290° C. for 6 h with constant stir rate. The reaction was allowed to cool to room temperature and the products were subjected to esterification in order to derivatize the remaining oleic acid to oleic acid methyl ester for analysis by GC-MS. In order to derivatize, the hexanes were removed under reduced pressure followed by the addition of HCl (1 M, 2 mL). The mixture was stirred for 1 h at 80° C. After cooling to room temperature, NaCl (1%, 1 mL) was added to the reaction mixture to increase the recovery of oleic acid methyl ester by solvent extraction. The ester of oleic acid was extracted with hexanes (3×3 mL) and was analyzed by GC-MS methyl nonadecanoate (C$_{19}$) as an internal standard.

Example 2.7

General Procedure for Integrated Batch Reaction, Also Called Sequential Sequestration-Catalysis In a typical two-step process, the catalyst (10 mg) was added to a test tube containing the oleic acid solution in hexanes (1 mM, 10 mL), mixed for 6 h and then the suspension was centrifuged. The amount sequestered was calculated by measuring the oleic acid remaining in the supernatant. In order to convert the sequestered oleic acid to liquid hydrocarbons, the catalyst remaining after centrifugation was mixed with 10 mL hexanes and the mixture was loaded into the reactor. After purging with H$_2$, the reaction mixture was kept at 290° C. and 450 psi for 6 h with constant stirring. The reaction was allowed to cool to room temperature and the liquid samples were analyzed by GC-MS using C$_{19}$ internal standard.

Example 2.8

Physiochemical Characterization and Activity of Ni-MSN and Ni$_2$P-MSN

Figure 10A:
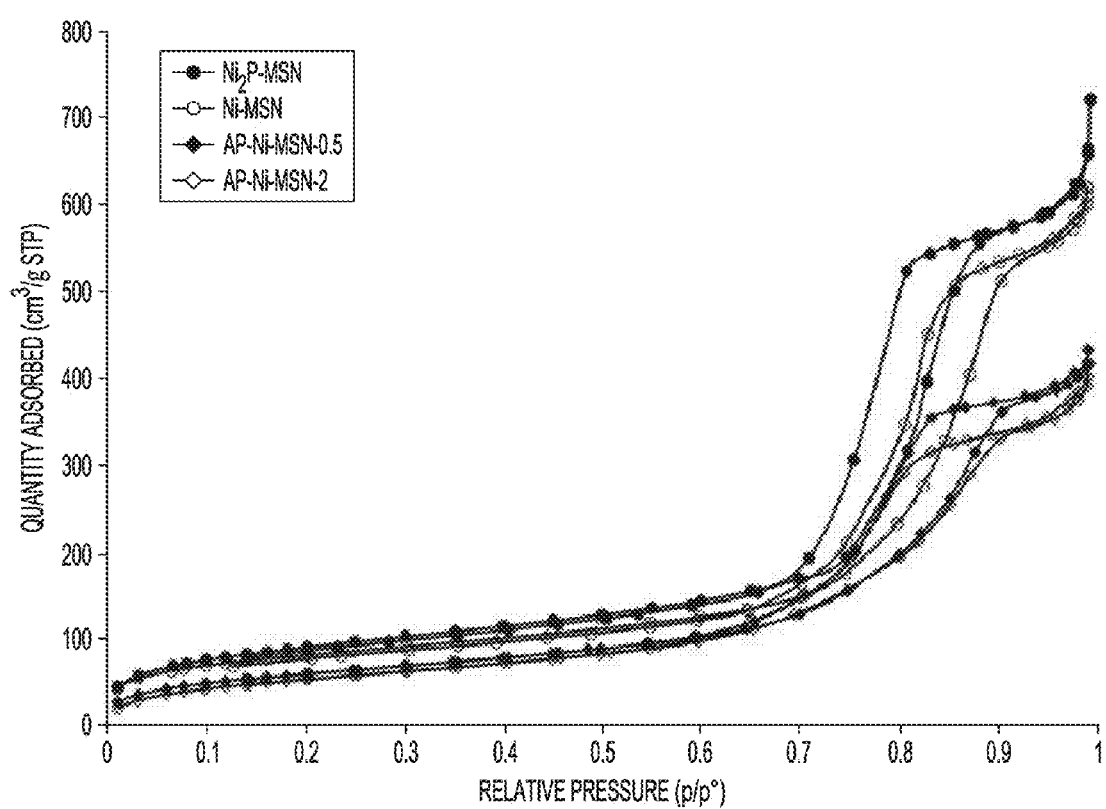
FIG. 10a illustrates BET isotherms of Ni$_2$P-MSN, Ni-MSN, AP-Ni-MSN-0.5, and AP-Ni-MSN-2, in accordance with various embodiments.
Figure 10B:
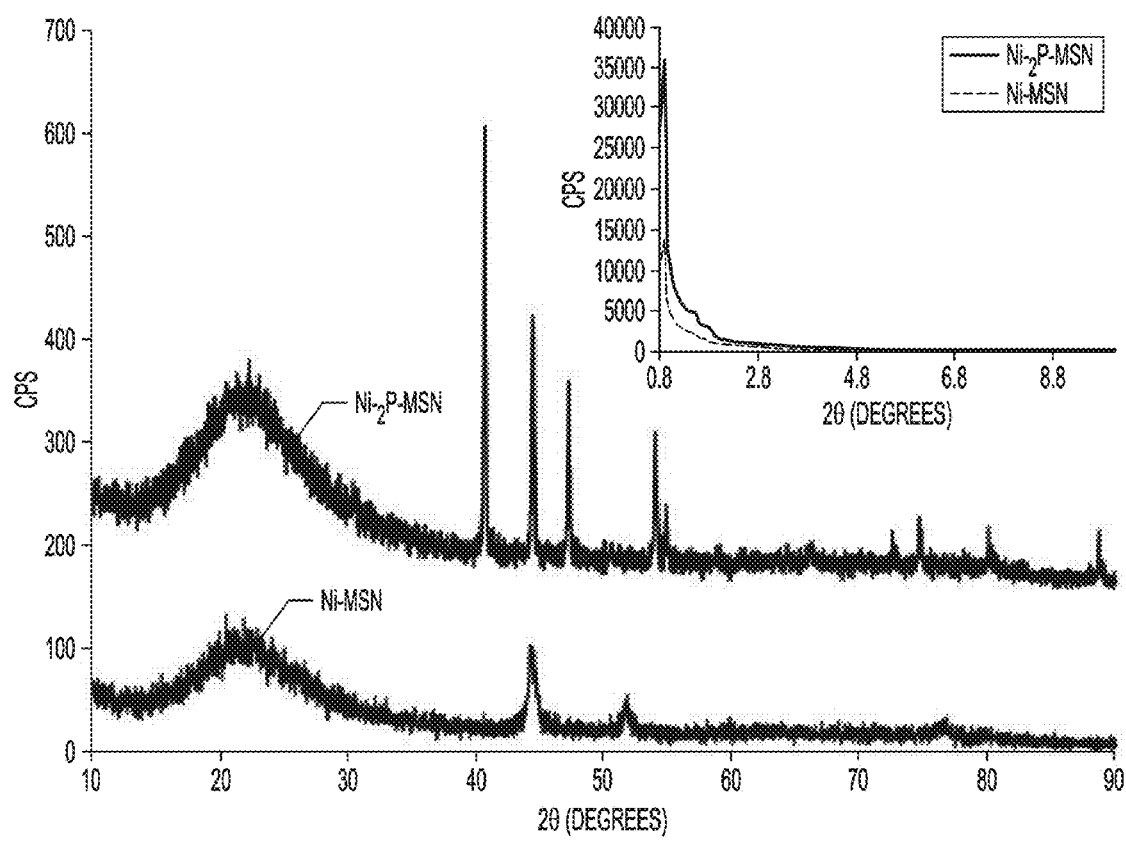
FIG. 10b illustrates X-ray diffraction patterns for Ni-MSN and Ni$_2$P-MSN, in accordance with various embodiments.
Figure 11A:
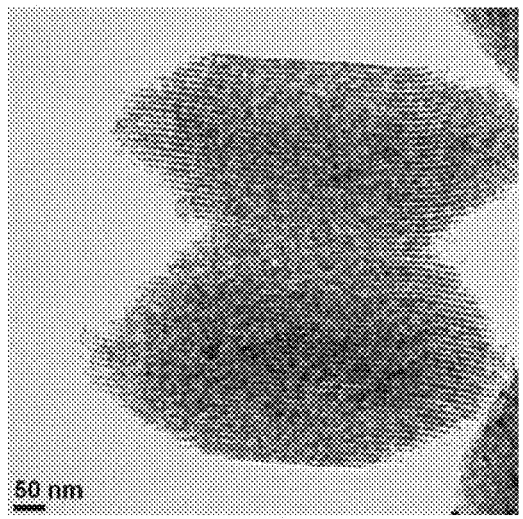
FIG. 11a illustrates a TEM image of Ni-MSN, in accordance with various embodiments.
Figure 11B:
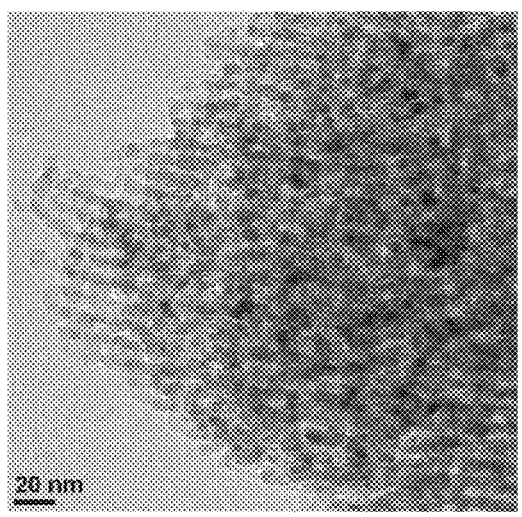
FIG. 11b illustrates a TEM image of Ni-MSN, in accordance with various embodiments.
Figure 11C:
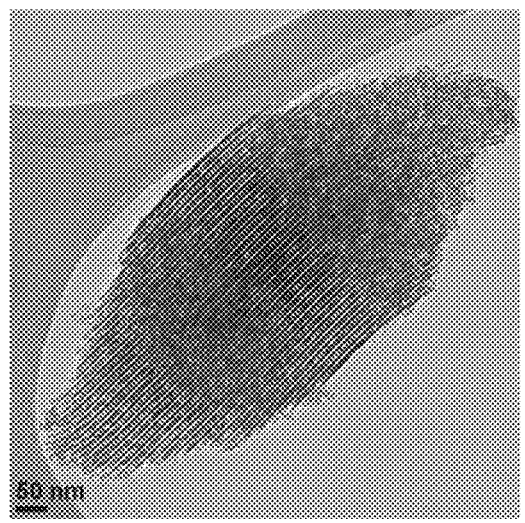
FIG. 11c illustrates a TEM image of Ni$_2$P-MSN, in accordance with various embodiments.

The textural properties of Ni-MSN and Ni$_2$P-MSN were obtained from nitrogen sorption analysis using BET and BJH calculations (FIG. 10a). FIG. 10a illustrates BET isotherms of Ni$_2$P-MSN, Ni-MSN, AP-Ni-MSN-0.5, and AP-Ni-MSN-2. Both materials possess type IV isotherms, which is characteristic of mesoporosity. The values for all the structural parameters are summarized in Table 2. FIG. 10b shows the X-ray diffraction pattern for Ni-MSN and Ni$_2$P-MSN, with the inset showing low angle XRD patterns and the larger plot showing wide angle XRD patterns. The observed diffraction patterns with intense (d$_{100}$) peaks are characteristic of highly ordered two-dimensional (2D) hexagonal mesostructures with uniform channels. The presence of (d$_{110}$) and (d$_{200}$) in both materials indicates that the structural order is maintained and suggests that both Ni and Ni$_2$P particles are evenly distributed inside the channels in the MSNs. The characteristic peaks of both Ni and Ni$_2$P in high angle X-ray diffraction confirm the formation of crystalline metallic nickel and Ni$_2$P phase (FIG. 10b) respectively. The homogeneous distribution of both Ni and Ni$_2$P particles in the channels of MSN was further confirmed by TEM-EDX images shown in FIGS. 11a and 11c, showing Ni-MSN and Ni$_2$P-MSN, respectively. FIG. 11b shows a zoomed-in view of FIG. 11a, more clearly showing particles of Ni in the MSN. As summarized in Table 2, after the formation of Ni and Ni$_2$P crystalline phase in the mesopores of MSN, both materials maintained similar structural properties. This provides evidence that the difference in the active catalytic phase (e.g., Ni and Ni$_2$P) may be responsible for the observed difference in catalytic activity.

TABLE 2

Summary of textural properties of catalysts.

| Sample | Surface area (m²/g) | Pore Volume (cm³/g) | Pore Size (nm) | Ni Loading (wt. %) | AP Loading (mmol/g) |
|---|---|---|---|---|---|
| Ni-MSN | 298 | 0.9 | 11 | 6.9 | 0 |
| Ni$_2$P-MSN | 317 | 1.0 | 11 | 5.2 | 0 |
| AP-Ni-MSN-0.5 | 227 | 0.6 | 9.1 | 6.6 | 0.5 |
| AP-Ni-MSN-2 | 209 | 0.6 | 8.9 | 6.5 | 2 |

As a reference reaction, the catalytic conversion of oleic acid was carried out at 290° C. and 30 bar H$_2$ for 6 hours in batch mode. Some of the possible reactions of the oleic acid reaction include cracking, hydrogenation, reduction, decarboxylation, and hydrodeoxygenation (Scheme 1).

Scheme 1. Reaction products.

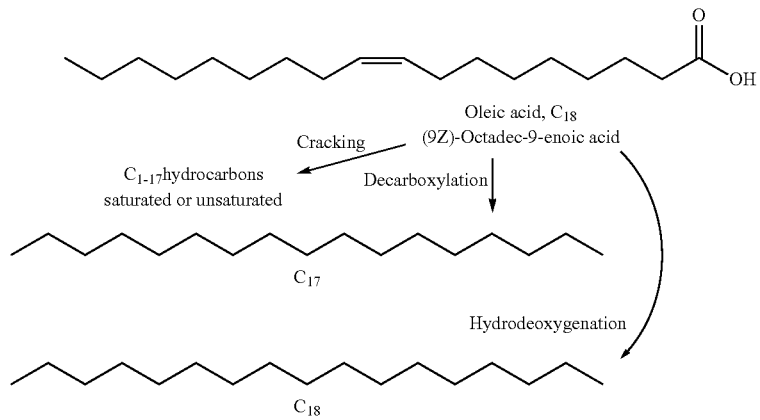

Figure 12:
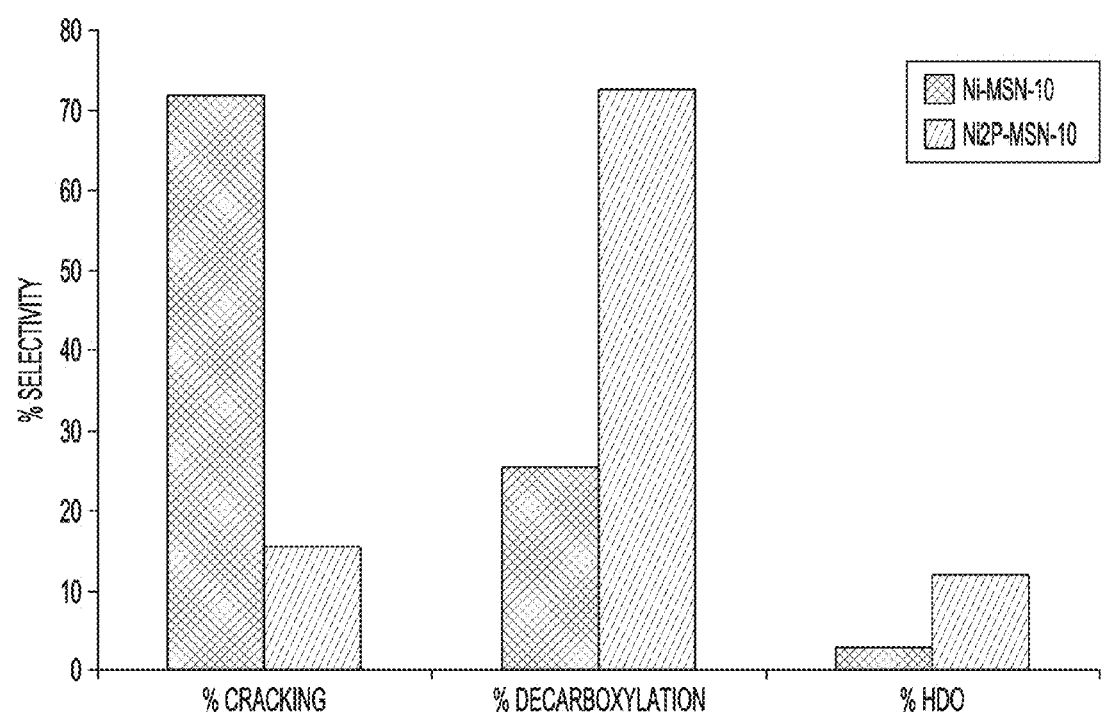
FIG. 12 illustrates the selectivities of Ni-MSN and Ni$_2$P-MSN catalyst for conversion of oleic acid, in accordance with various embodiments.

The observed selectivities while using Ni-MSN and Ni$_2$P-MSN catalyst for conversion of oleic acid are shown in FIG. 12. Ni-MSN led to selectivities of 72% cracking, 25% decarboxylation and 3% HDO while the selectivities of cracking decreased by approximately five fold to 15% and that of decarboxylation of oleic acid to heptadecane (C$_{17}$) increased almost by three fold to 73% with Ni$_2$P-MSN catalyst. In addition, the selectivity for hydrodeoxygenation of oleic acid to octadecane (C$_{18}$) increased by four fold to 12% using Ni$_2$P-MSN as a catalyst.

Example 2.9

Sequestration of Oleic Acid by Ni-MSN and AP-Ni-MSN

Figure 13A:
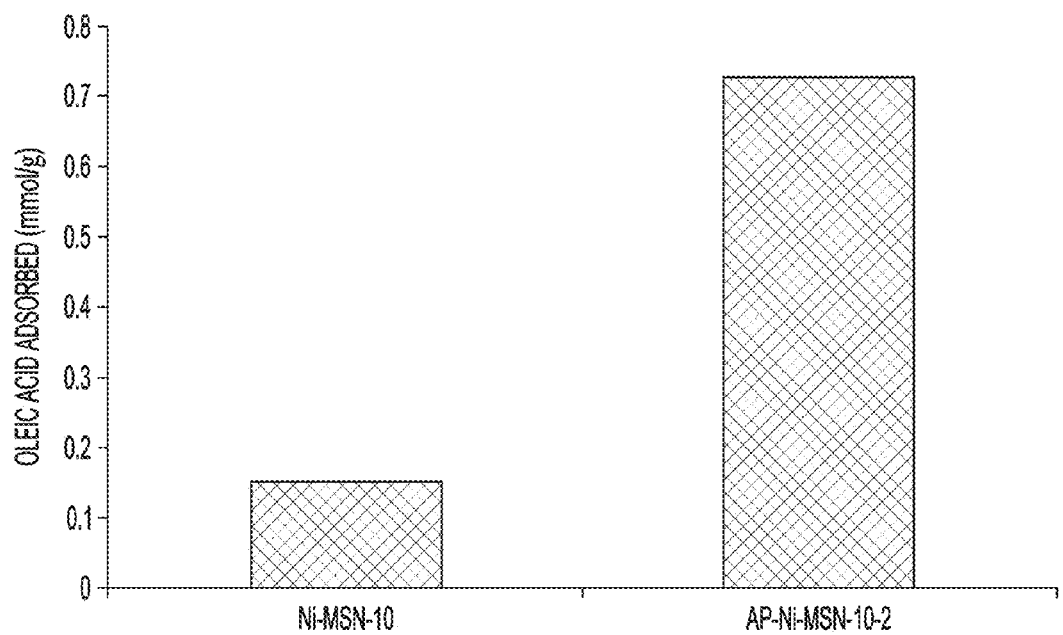
FIG. 13a illustrates a comparison of the sequestration of oleic acid using Ni-MSN-10 and AP-Ni-MSN-10-2, in accordance with various embodiments.

Free fatty acids can be sequestered using 3-aminopropyl trimethoxysilane functionalized MSN (AP-MSN). In order to increase the proximity and concentrate oleic acid near Ni particles in the channels of Ni-MSN, amino propyl group was functionalized on the surface of Ni-MSN to obtain AP-Ni-MSN-2 material. While the maintenance of pore structure was confirmed by nitrogen sorption analysis, as shown in FIG. 10a, a small decrease in pore volume (0.9 cm³/g to 0.6 cm³/g) and pore size (11 nm to 8.9 nm) along with a drop in surface area (298 m²/g to 209 m²/g) was observed after functionalization. Despite the loss in surface area, AP-Ni-MSN-2 sequestered 73% of available oleic acid (0.73 mmol oleic acid/g of material from a 1.0 mM oleic acid solution) compared to 15% (0.15 mmol oleic acid/g of material) by Ni-MSN, as shown in FIG. 13a.

Figure 13B:
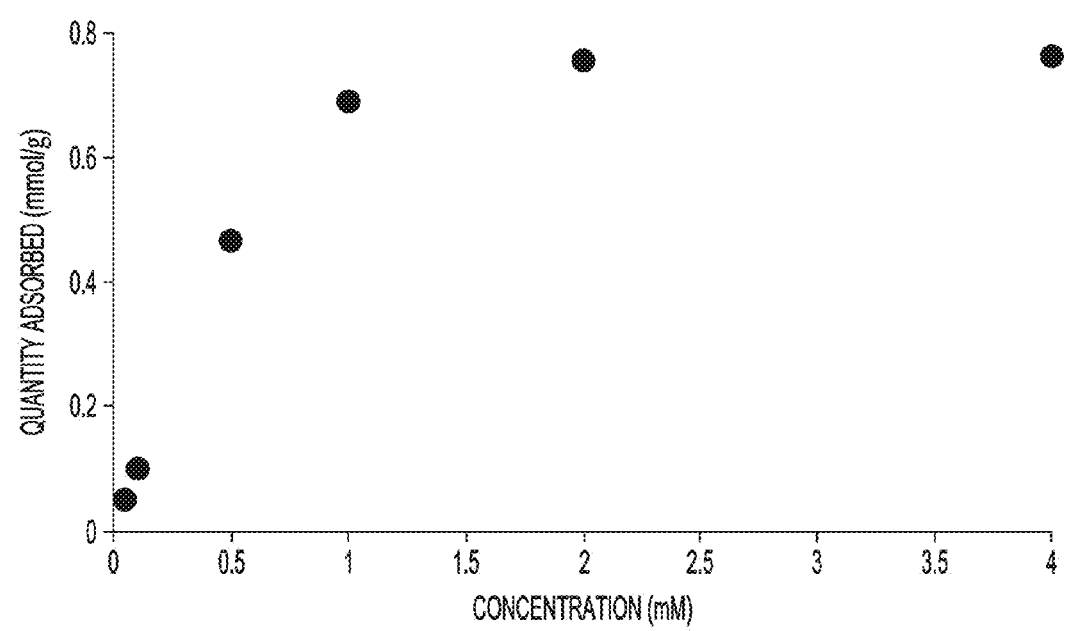
FIG. 13b illustrates the sequestration of oleic acid at various concentrations using AP-Ni-MSN-10-2, in accordance with various embodiments.
Figure 13C:
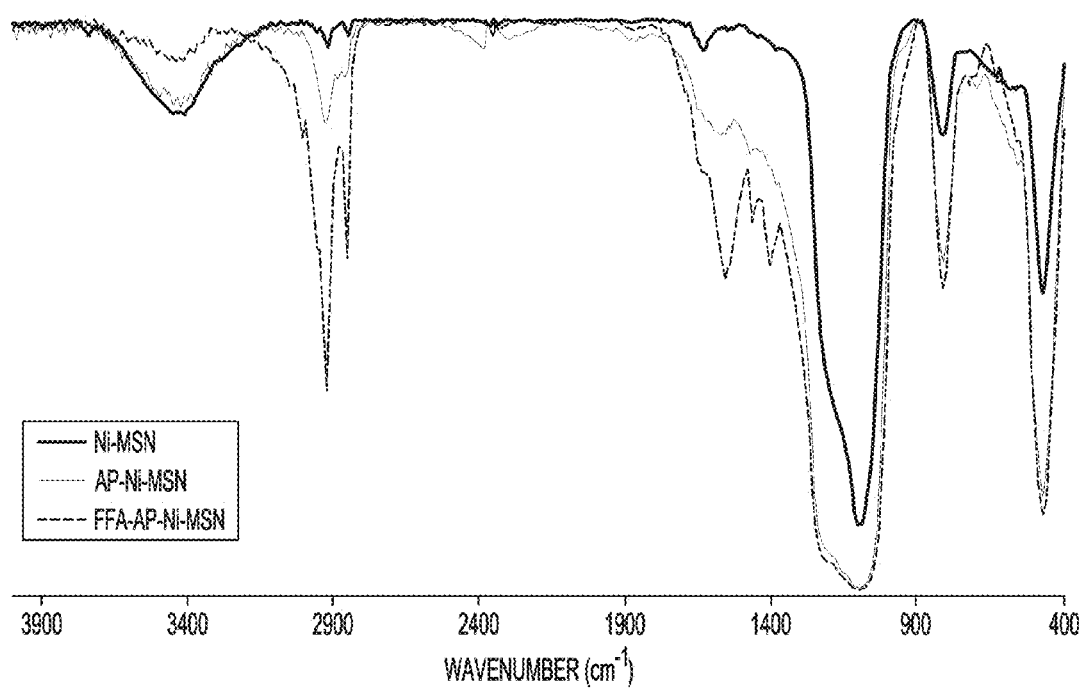
FIG. 13c illustrates the infrared spectra of Ni-MSN, AP-Ni-MSN, and oleic acid-adsorbed AP-Ni-MSN, in accordance with various embodiments.

To further examine the sequestration capacity, AP-Ni-MSN (10 mg) was mixed with the varying concentration of oleic acid for 6 h. The amount of oleic acid sequestered by AP-Ni-MSN sharply increased at lower concentrations and eventually plateaued at higher concentrations with maximum adsorption of 0.76 mmol oleic acid g$^{-1}$ of adsorbent (FIG. 13b). The sequestration of oleic acid by AP-Ni-MSN was confirmed by the presence of sharp C—H stretching bands at 2926 cm$^{-1}$ and 2850 cm$^{-1}$ as well as the two assymetrical and symmetrical carboxylate vibrations at 1558 cm$^{-1}$ and 1403 cm$^{-1}$ respectively (FIG. 13c). Whether the sequestration capacity of AP-Ni-MSN could impose a synergistic effect during catalysis by increasing the local concentration of oleic acid near the Ni catalytic site was examined in subsequent Examples.

Example 2.10

Effect of Amine Functionalization on Catalytic Activity

Figure 14:
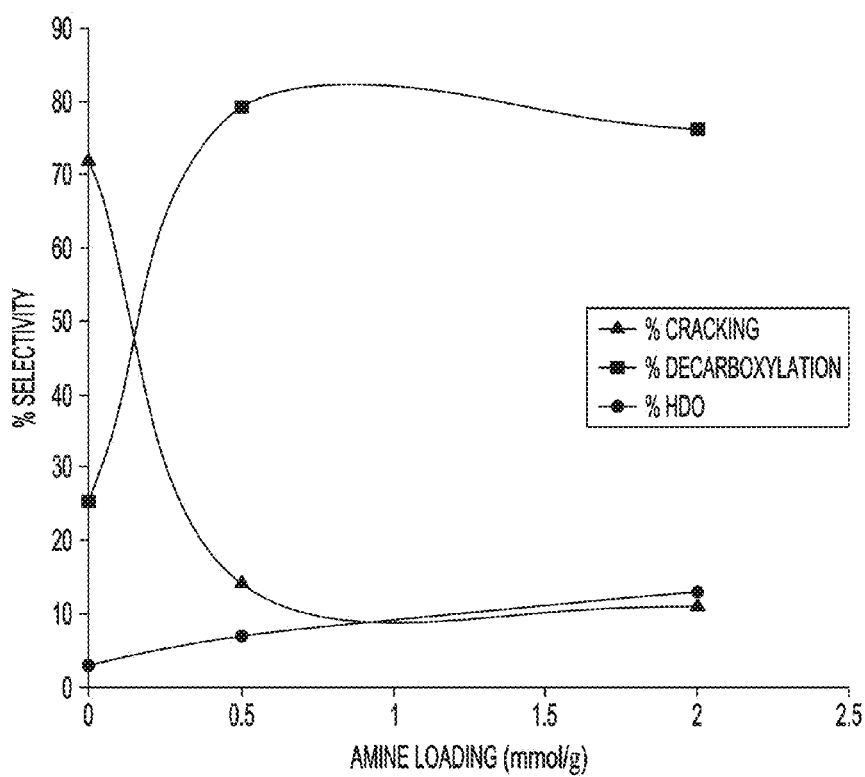
FIG. 14 illustrates the percent selectivity of Ni-MSN having various levels of amine loading toward various reactions, in accordance with various embodiments.
Figure 15:
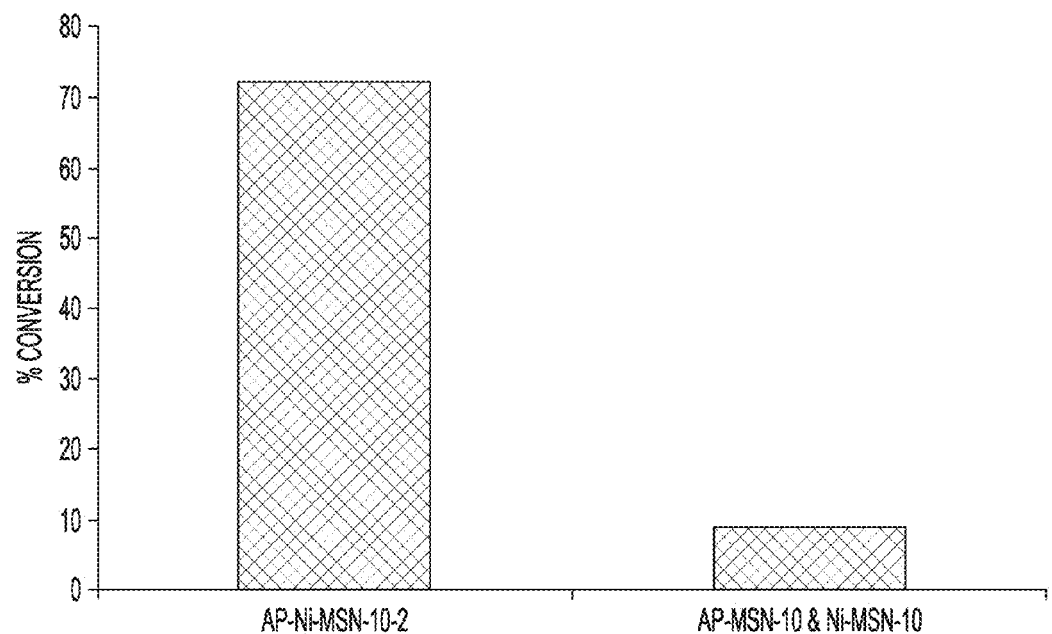
FIG. 15 illustrates the percent conversion of oleic acid when a mixture of AP-MSN and Ni-MSN was used, in accordance with various embodiments.

To explore the effect of amine functionalization on catalytic conversion of oleic acid, Ni-MSN with different loading of amino propyl group (0.5 mmol/g Ni-MSN and 2 mmol/g Ni-MSN) was synthesized. These two materials were denoted as AP-Ni-MSN-0.5 and AP-Ni-MSN-2 respectively and possessed similar textural properties as shown in Table 2 and FIG. 10. Functionalization of amine led to decrease in selectivity of cracking from 72% by Ni-MSN to 14% by AP-Ni-MSN-0.5 and increase in decarboxylation and HDO selectivity to 79% and 7% respectively, compared to Ni-MSN. Further decrease in O:C ratio of the product was obtained by increasing the loading of amino functional group on Ni-MSN, e.g., the selectivity toward C$_{18}$ via HDO was two times more for AP-Ni-MSN-2 catalyst compared to AP-Ni-MSN-0.5, as shown in FIG. 14. These enhancements for simultaneous sequestration-catalysis is may be due to the proximity of an amino group and Ni catalytic site. The amino group can concentrate the oleic acid near the Ni sites for a synergistic catalytic effect. When the physical mixture of amine functionalized mesoporous silica nanoparticle (AP-MSN) and Ni-MSN was used as catalyst, only 9% of available oleic acid was converted to hydrocarbons (FIG. 15). This suggests that the kinetics of oleic acid sequestration by AP-MSN is faster than its conversion to hydrocarbons by Ni catalyst and the interaction between amino group and the carboxylic acid is strong even at high temperatures. Moreover, AP-Ni-MSN-2 catalyst was as active as $Ni_2P$-MSN, which showed less cracking and higher $C_{17}$ and $C_{18}$ yield.

Example 2.11

Enhancement of HDO Selectivity by Integrated Sequestration-Catalysis Approach

Figure 16:
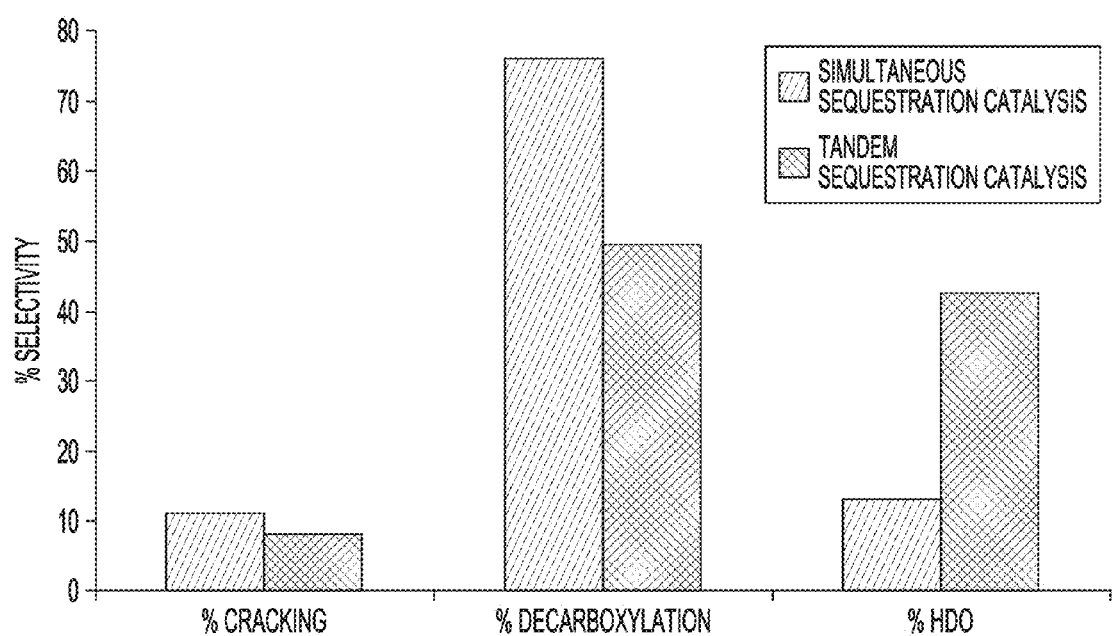
FIG. 16 illustrates the percent selectivity of AP-Ni-MSN-2 catalyst toward various reactions, according to various embodiments.

It was hypothesized that if the residence time of oleic acid near the active Ni catalyst in the mesopores is increased before the catalysis, the chemical processing of oleic acid in the reaction condition should be different than the simultaneous sequestration-catalysis approach discussed earlier. In order to test this hypothesis, at first the oleic acid was sequestered by AP-Ni-MSN-2 catalyst at ambient condition by shaking. The catalyst was separated, air dried and suspended in hexane, which was then processed at reaction condition. Unexpectedly, as compared to the simultaneous sequestration-catalysis method, the HDO selectivity (e.g., $C_{18}$ yield) increased by three-fold with tandem sequestration-catalysis approach, as shown in FIG. 16. To the best of our knowledge, this type of sorbent assisted catalysis has not been explored before. This Example demonstrates that the adsorbent-functionalized catalyst-containing MSN can increase the C:O ratio of a mixture as evident by the increase in $C_{17}$ and $C_{18}$ hydrocarbons, compared to a catalyst not functionalized with adsorbent groups.

Example 2.12

Selective Sequestration and Hydrotreatment of Microalgae Oil with AP-Ni-MSN

In green diesel production, the basic catalysts used for the tranesterification of oils with short-chain alcohols can be neutralized by free fatty acids (FFAs), forming soap. Removal of FFAs by selective sequestration on magnetic nanomaterials such as AP-Ni-MSN can provide a valuable alternative environmentally friendly method at least in part due to room temperature adsorption process and separation by magnetic decantation. Moreover, the integration of both aminopropyl functional groups for sequestration of FFAs and magnetic Ni-MSN catalyst for conversion of FFAs to liquid hydrocarbon fuels can be a remarkable alternative for downstream processing of FFA-rich renewable feedstocks for bio-fuel production.

Figure 17A:
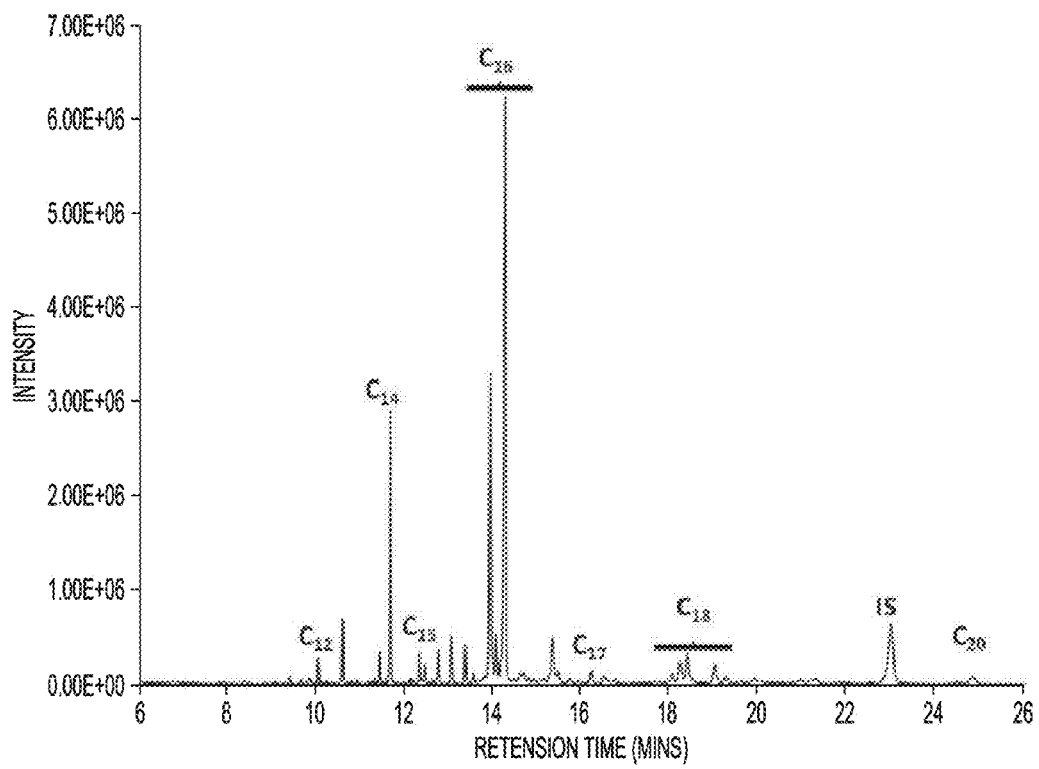
FIG. 17a illustrates the concentration of various fatty acids extracted from microalgae, in accordance with various embodiments.
Figure 17B:
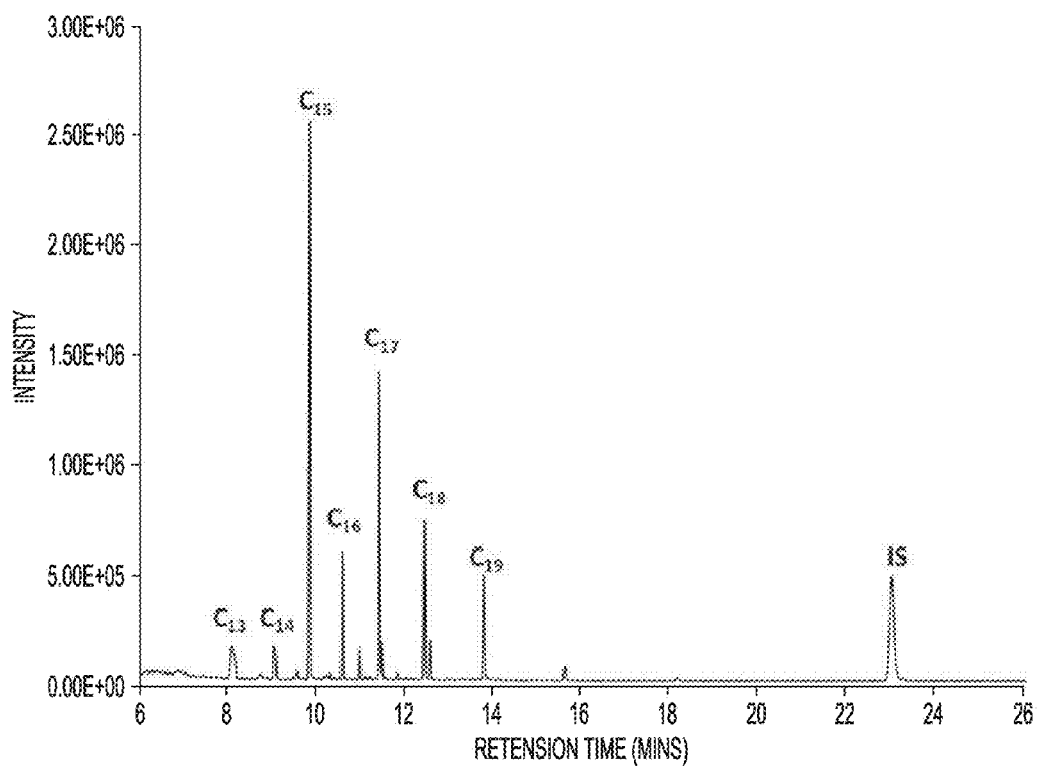
FIG. 17b illustrates the concentration of various hydrocarbons formed by hydrotreating fatty acids sequestered from microalgae using AP-Ni-MSN, in accordance with various embodiments.

The microalgae extract in hexanes was first analyzed to ascertain the presence of FFAs. The chain length of FFAs detected in microalgae extract ranges from $C_{12}$ to $C_{20}$ as shown in the FFA profile of microalgae extract in FIG. 17a. The FFAs from these microalgae extract (10 mL) were sequestered with AP-Ni-MSN (10 mg) and subsequently treated at reaction condition for integrated batch reaction. It was demonstrated that 47 wt % of available FFA in microalgae extract was sequestered by AP-Ni-MSN and 66% of the sequestered FFA were converted to liquid hydrocarbons (Table 3). It should be noted that the FFA composition of microalgae extract mostly comprises saturated $C_{16}$ fatty acids (50 wt %) and unsaturated $C_{16}$ fatty acids (30 wt %). Moreover, the fatty acid with $C_{16}$ chain length is also the most sequestered FFAs (68 wt %). As shown in FIG. 17b, n-pentadecane is the major liquid hydrocarbon obtained because of the decarboxylation of sequestered $C_{16}$ FFAs with integrated AP-Ni-MSN catalyst.

TABLE 3

Integrated sequestration catalysis.

| Amount of FFAs present (mg · $L^{-1}$) | Amount of FFAs extracted (mg · $g^{-1}$ of AP-Ni-MSN) | Amount of hydrocarbons (mg · $g^{-1}$ of AP-Ni-MSN) |
| --- | --- | --- |
| 413 | 195 | 95.3 |

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by specific embodiments and optional features, modification and variation of the concepts herein disclosed may be resorted to by those of ordinary skill in the art, and that such modifications and variations are considered to be within the scope of this invention as defined by the appended claims.

Additional Embodiments

The present invention provides for the following exemplary embodiments, the numbering of which is not to be construed as designating levels of importance:

Embodiment 1 provides a method comprising: combining a catalyst with at least one first molecule comprising at least one of a fatty acid, a fatty acid ester, a monoglyceride, a diglyceride, and a triglyceride, to provide a mixture, the catalyst comprising a mesoporous silica nanoparticle comprising a catalytic material comprising iron; and combining the mixture with a hydrogen gas under conditions so that the catalytic material in the catalyst catalyzes a chemical transformation of the first molecule.

Embodiment 2 provides the method of Embodiment 1, wherein a pressure of the hydrogen is controlled to be about 1 bar to about 1000 bar.

Embodiment 3 provides the method of any one of Embodiments 1-3, wherein a pressure of the hydrogen is controlled to be about 10 bar to about 100 bar.

Embodiment 4 provides the method of any one of Embodiments 1-4, wherein a temperature of the mixture is controlled to about 150° C. to about 1000° C.

Embodiment 5 provides the method of any one of Embodiments 1-5, wherein a temperature of the mixture is controlled to be about 250° C. to about 350° C.

Embodiment 6 provides the method of any one of Embodiments 1-6, wherein the chemical transformation of the first molecule comprises hydrotreatment.

Embodiment 7 provides the method of any one of Embodiments 1-7, wherein combining the catalyst with the first molecule comprises combining the catalyst with a solution comprising the first molecule, to provide the mixture.

Embodiment 8 provides the method of any one of Embodiments 1-8, wherein the fatty acid is a $C_{5-50}$ fatty acid.

Embodiment 9 provides the method of any one of Embodiments 1-9, further comprising separating the catalyst from the mixture.

Embodiment 10 provides the method of Embodiment 9, comprising at least one of using and selling the separated mixture as a feedstock for generating green diesel.

Embodiment 11 provides the method of any one of Embodiments 1-10, wherein the catalytic material has a particle size equal to or less than a pore size of the catalytic material.

Embodiment 12 provides the method of any one of Embodiments 1-11, wherein the catalytic material has a particle size of about 5 nm to about 15 nm.

Embodiment 13 provides the method of any one of Embodiments 1-12, wherein the catalytic material has a particle size of about 8 nm to about 13 nm.

Embodiment 14 provides the method of any one of Embodiments 1-13, wherein the catalytic material is a hydrotreatment catalyst.

Embodiment 15 provides the method of any one of Embodiments 1-14, wherein the catalytic material comprises at least one of a cracking catalyst, a hydrogenation catalyst, a decarboxylation catalyst, and a hydrodeoxygenation catalyst.

Embodiment 16 provides the method of any one of Embodiments 1-15, wherein the catalytic material further comprises at least one of nickel, nickel phosphide, rhodium, ruthenium, gold, cobalt, cobalt oxide, palladium, platinum, and molybdenum.

Embodiment 17 provides the method of any one of Embodiments 1-16, wherein the catalytic material is located at least partially within pores of the mesoporous silica nanoparticle.

Embodiment 18 provides the method of any one of Embodiments 1-17, wherein the catalytic material is approximately evenly distributed within the pores of the mesoporous silica nanoparticle.

Embodiment 19 provides the method of any one of Embodiments 1-18, wherein the catalytic material is crystalline.

Embodiment 20 provides the method of any one of Embodiments 1-19, wherein about 0.1 wt % to about 30 wt % of the catalyst comprises the catalytic material.

Embodiment 21 provides the method of any one of Embodiments 1-20, wherein the catalyst comprises about 0.1 wt % to about 30 wt % iron or a compound thereof.

Embodiment 22 provides the method of any one of Embodiments 1-21, wherein the catalyst comprises about 1 wt % to about 10 wt % iron or a compound thereof.

Embodiment 23 provides the method of any one of Embodiments 1-22, wherein the catalyst has a particle size of about 50 nm-1200 nm.

Embodiment 24 provides the method of any one of Embodiments 1-23, wherein the catalyst has a surface area of about 100 $m^2/g$-1000 $m^2/g$.

Embodiment 25 provides the method of any one of Embodiments 1-24, wherein the catalyst has a surface area of about 150 $m^2/g$ to about 375 $m^2/g$.

Embodiment 26 provides the method of any one of Embodiments 1-25, wherein the catalyst has a pore size of about 5 nm to about 15 nm.

Embodiment 27 provides the method of any one of Embodiments 1-26, wherein the catalyst has a pore size of about 8 nm to about 13 nm.

Embodiment 28 provides the method of any one of Embodiments 1-27, wherein the catalyst has a pore volume of about 0.1 $cm^3/g$ to about 5 $cm^3/g$.

Embodiment 29 provides the method of any one of Embodiments 1-28, wherein the catalyst has a pore volume of about 0.5 $cm^3/g$ to about 1.5 $cm^3/g$.

Embodiment 30 provides the method of any one of Embodiments 1-29, wherein the catalyst is magnetic.

Embodiment 31 provides the method of any one of Embodiments 1-30, wherein the catalyst comprises at least one of $Fe_2O_3$ and $Fe_3O_4$.

Embodiment 32 provides the method of any one of Embodiments 1-31, wherein the catalyst comprises an ordered silicon oxide matrix with hexagonal symmetry.

Embodiment 33 provides the method of any one of Embodiments 1-32, wherein the first molecule is a fatty acid.

Embodiment 34 provides the method of any one of Embodiments 1-33, wherein the fatty acid is a ($C_5$-$C_{50}$) fatty acid.

Embodiment 35 provides the method of any one of Embodiments 1-34, wherein the fatty acid is oleic acid.

Embodiment 36 provides a method comprising: combining an adsorbent catalyst with at least one first molecule comprising at least one of a fatty acid, a fatty acid ester, a monoglyceride, a diglyceride, and a triglyceride, to provide a mixture; wherein the adsorbent catalyst comprises a mesoporous silica nanoparticle comprising a catalytic material comprising iron and at least one adsorbent functional group comprising a functional group selected from the group consisting of an amino($C_1$-$C_{20}$)alkyl group or a salt thereof, a ($C_1$-$C_{20}$)alkyl carboxylic acid group or a salt thereof, a ($C_1$-$C_{20}$)alkyl sulfonic acid group or a salt thereof, and a perfluoro($C_1$-$C_{20}$)alkyl group, wherein the alkyl unit of the aminoalkyl group, the alkyl carboxylic acid group, the alkyl sulfonic acid group, and of the perfluoroalkyl group is covalently bound to the mesoporous silica nanoparticle, and wherein the $C_1$-$C_{20}$ alkyl groups of the amino($C_1$-$C_{20}$)alkyl group are independently optionally interrupted by one or two —NH— groups.

Embodiment 37 provides the method of Embodiment 36, wherein the first molecule is selectively adsorbed by the adsorbent functional group.

Embodiment 38 provides the method of any one of Embodiments 36-37, further comprising combining the mixture with a first reagent, under conditions so that the catalytic material in the adsorbent catalyst catalyzes a chemical transformation of the first molecule.

Embodiment 39 provides the method of Embodiment 38, wherein combining the adsorbent catalyst with the first molecule comprises combining the adsorbent catalyst with a solution comprising the first molecule, to provide the mixture.

Embodiment 40 provides the method of Embodiment 39, wherein the solution further comprises at least one second molecule that is at least one of a) not adsorbed by the adsorbent functional group and b) adsorbed by the adsorbent functional group at a lower rate than the first molecule is adsorbed by the adsorbent functional group.

Embodiment 41 provides the method of Embodiment 40, wherein the first molecule is a fatty acid and the second molecule is at least one of a fatty acid ester and a triglyceride.

Embodiment 42 provides the method of any one of Embodiments 40-41, wherein first molecule is a fatty acid and the second molecule is at least one of a $C_{5-50}$ fatty acid $C_{1-50}$ ester and a triglyceride having $C_{5-50}$ fatty acid groups.

Embodiment 43 provides the method of any one of Embodiments 37-42, comprising separating the adsorbent catalyst having the first molecule adsorbed thereto from the mixture.

Embodiment 44 provides the method of Embodiment 43, comprising at least one of using and selling the separated mixture as a feedstock for generating green diesel.

Embodiment 45 provides the method of any one of Embodiments 43-44, comprising combining the separated adsorbent catalyst with a first reagent under conditions so that the catalytic material in the adsorbent catalyst catalyzes a chemical transformation of the first molecule.

Embodiment 46 provides the method of Embodiment 45, wherein the first reagent comprises hydrogen gas.

Embodiment 47 provides the method of Embodiment 46, comprising controlling a pressure of the hydrogen to be about 1 bar to about 1000 bar.

Embodiment 48 provides the method of any one of Embodiments 46-47, comprising controlling a pressure of the hydrogen to be about 10 bar to about 100 bar.

Embodiment 49 provides the method of any one of Embodiments 46-48, comprising controlling a temperature of the combined separated adsorbent catalyst and the hydrogen to be about 150° C. to about 1000° C.

Embodiment 50 provides the method of any one of Embodiments 46-49, comprising controlling a temperature of the combined separated adsorbent catalyst and the hydrogen to be about 250° C. to about 350° C.

Embodiment 51 provides the method of any one of Embodiments 45-50, wherein the chemical transformation of the first molecule comprises at least one of cracking, reduction, hydrogenation, decarboxylation, and hydrodeoxygenation.

Embodiment 52 provides the method of Embodiment 51, comprising at least one of using and selling a product of the chemical transformation of the first molecule as a fuel.

Embodiment 53 provides a method comprising: combining at least one adsorbent catalyst with a solution comprising a fatty acid and at least one of a fatty acid ester and a triglyceride, to provide a mixture, the adsorbent catalyst comprising at least one adsorbent functional group comprising a functional group selected from the group consisting of an amino($C_1$-$C_{20}$)alkyl group or a salt thereof, a ($C_1$-$C_{20}$) alkyl carboxylic acid group or a salt thereof, a ($C_1$-$C_{20}$)alkyl sulfonic acid group or a salt thereof, and a perfluoro($C_1$-$C_{20}$)alkyl group, wherein the alkyl unit of the aminoalkyl group, the alkyl carboxylic acid group, the alkyl sulfonic acid group, and of the perfluoroalkyl group is covalently bound to a mesoporous silica nanoparticle, and wherein the $C_1$-$C_{20}$ alkyl groups of the amino($C_1$-$C_{20}$)alkyl group are independently optionally interrupted by one or two —NH— groups; and a catalytic material comprising iron; separating the adsorbent catalyst having the first molecule adsorbed thereto from the mixture; and combining the separated adsorbent catalyst with hydrogen gas so that the catalytic material in the adsorbent catalyst catalyzes a chemical transformation of the fatty acid comprising at least one of cracking, hydrogenation, reduction, decarboxylation, and hydrodeoxygenation.

Embodiment 54 provides a catalyst comprising: a mesoporous silica nanoparticle; and a catalytic material comprising iron nanoparticles; wherein the iron nanoparticles are at least partially within pores of the mesoporous silica nanoparticle.

Embodiment 55 provides the catalyst of Embodiment 54, wherein the catalyst is sufficient to catalyze hydrocracking in the presence of $H_2$ at a lower rate than the catalyst catalyzes at least one of hydrogenation, reduction, decarboxylation, and hydrodeoxygenation.

Embodiment 56 provides the catalyst of any one of Embodiments 54-55, wherein the catalyst is sufficient to catalyze hydrocracking of a ($C_5$-$C_{50}$) fatty acid in the presence of $H_2$ at a lower rate than the catalyst catalyzes at least one of hydrogenation, reduction, decarboxylation, and hydrodeoxygenation.

Embodiment 57 provides the catalyst of any one of Embodiments 54-56, wherein the catalyst is sufficient to catalyze hydrocracking of a ($C_5$-$C_{50}$) fatty acid in the presence of $H_2$ such that, at about 100% conversion of the fatty acid, at a temperature of about 200° C. to about 400° C., about 0.01-15% of the yield of the reaction is hydrocracking product.

Embodiment 58 provides the catalyst of any one of Embodiments 54-57, wherein the catalyst is sufficient to catalyze hydrocracking of a ($C_5$-$C_{50}$) fatty acid in the presence of $H_2$ such that, at about 100% conversion of the fatty acid, at a temperature of about 200° C. to about 350° C., less than about 10% of the yield of the reaction is hydrocracking product.

Embodiment 59 provides the catalyst of any one of Embodiments 54-58, wherein the catalyst is sufficient to catalyze hydrocracking of a ($C_5$-$C_{50}$) fatty acid in the presence of $H_2$ such that, at about 100% conversion of the fatty acid, at a temperature of about 200° C. to about 350° C., less than about 5% of the yield of the reaction is hydrocracking product.

Embodiment 60 provides the catalyst of any one of Embodiments 54-59, wherein the catalyst is sufficient to catalyze hydrotreatment of a ($C_5$-$C_{50}$) fatty acid in the presence of $H_2$ such that about 100% conversion of the fatty acid occurs in about 1 h to about 20 h at a temperature of about 200° C. to about 400° C.

Embodiment 61 provides the catalyst of any one of Embodiments 54-60, wherein the catalyst is sufficient to catalyze hydrotreatment of a ($C_5$-$C_{50}$) fatty acid in the presence of $H_2$ such that about 100% conversion of the fatty acid occurs in about 1 h to about 10 h at a temperature of about 200° C. to about 350° C.

Embodiment 62 provides the catalyst of any one of Embodiments 54-61, wherein the catalyst is sufficient to catalyze hydrotreatment of a ($C_5$-$C_{50}$) fatty acid in the presence of $H_2$ such that about 100% conversion of the fatty acid occurs in about 1 h to about 7 h at a temperature of about 200° C. to about 350° C.

Embodiment 63 provides the catalyst of any one of Embodiments 54-62, wherein the catalyst is sufficient to catalyze at least one of hydrogenation, reduction, decarboxylation, and hydrodeoxygenation of at least one of a $C_{5\text{-}50}$ fatty acid $C_{1\text{-}50}$ ester and a triglyceride having $C_{5\text{-}50}$ fatty acid groups in the presence of $H_2$ at a temperature of about 200° C. to about 400° C.

Embodiment 64 provides the catalyst of any one of Embodiments 54-63, further comprising at least one adsorbent functional group comprising a functional group selected from the group consisting of an amino($C_1$-$C_{20}$)alkyl group or a salt thereof, a ($C_1$-$C_{20}$)alkyl carboxylic acid group or a salt thereof, a ($C_1$-$C_{20}$)alkyl sulfonic acid group or a salt thereof, and a perfluoro($C_1$-$C_{20}$)alkyl group, wherein the alkyl unit of the aminoalkyl group, the alkyl carboxylic acid group, the alkyl sulfonic acid group, and of the perfluoroalkyl group is covalently bound to the mesoporous silica nanoparticle, wherein the $C_1$-$C_{20}$ alkyl groups of the amino ($C_1$-$C_{20}$)alkyl group are independently optionally interrupted by one or two —NH— groups, and wherein the catalyst is an adsorbent catalyst.

Embodiment 65 provides the adsorbent catalyst of Embodiment 64, wherein the adsorbent functional group adsorbs fatty acids at a higher rate than it adsorbs at least one of fatty acid esters and triglycerides.

Embodiment 66 provides the adsorbent catalyst of any one of Embodiments 64-65, wherein the adsorbent functional group comprises at least one of an amino($C_{1-10}$)alkyl group and a salt thereof wherein the alkyl unit is covalently bound to the mesoporous silica nanoparticle.

Embodiment 67 provides the adsorbent catalyst of any one of Embodiments 64-66, wherein the adsorbent functional group comprises at least one of an aminopropyl group and a salt thereof wherein the propyl unit is covalently bound to the mesoporous silica nanoparticle.

Embodiment 68 provides the adsorbent catalyst of any one of Embodiments 64-67, wherein the adsorbent functional group is present in a concentration of about 0.01 mmol to about 50 mmol per gram of the mesoporous silica nanoparticle.

Embodiment 69 provides the adsorbent catalyst of any one of Embodiments 64-68, wherein the adsorbent functional group is present in a concentration of about 0.1 mmol to about 15 mmol per gram of the mesoporous silica nanoparticle.

Embodiment 70 provides the adsorbent catalyst of any one of Embodiments 64-69, wherein the adsorbent catalyst is sufficient to catalyze decarboxylation and hydrodeoxygenation of a fatty acid at a higher rate than a corresponding mesoporous silica nanoparticle not having the adsorbent functional group bound thereto.

Embodiment 71 provides the adsorbent catalyst of any one of Embodiments 64-70, wherein the adsorbent catalyst is sufficient to catalyze cracking of a fatty acid at a lower rate than a corresponding mesoporous silica nanoparticle not having the adsorbent functional group bound thereto.

Embodiment 72 provides the adsorbent catalyst of any one of Embodiments 64-71, wherein the adsorbent functional group is present in a concentration of at least about 0.5 mmol per gram of the mesoporous silica nanoparticle.

Embodiment 73 provides the adsorbent catalyst of any one of Embodiments 64-72, wherein a percent selectivity of the adsorbent catalyst toward catalyzation of cracking of a fatty acid is about 10% to about 30% of a selectivity toward catalyzation of cracking of the fatty acid of a corresponding mesoporous silica nanoparticle including the catalytic material but not having the adsorbent functional group bound thereto.

Embodiment 74 provides the adsorbent catalyst of any one of Embodiments 64-73, wherein a percent selectivity of the adsorbent catalyst toward catalyzation of cracking of a fatty acid is about 15% to about 25% of a selectivity toward catalyzation of cracking of the fatty acid of a corresponding mesoporous silica nanoparticle including the catalytic material but not having the adsorbent functional group bound thereto.

Embodiment 75 provides the adsorbent catalyst of any one of Embodiments 64-74, wherein a percent selectivity of the adsorbent catalyst toward catalyzation of decarboxylation of a fatty acid is about 200% to about 400% of a selectivity toward catalyzation of decarboxylation of the fatty acid of a corresponding mesoporous silica nanoparticle including the catalytic material but not having the adsorbent functional group bound thereto.

Embodiment 76 provides the adsorbent catalyst of any one of Embodiments 64-75, wherein a percent selectivity of the adsorbent catalyst toward catalyzation of decarboxylation of a fatty acid is about 250% to about 350% of a selectivity toward catalyzation of decarboxylation of the fatty acid of a corresponding mesoporous silica nanoparticle including the catalytic material but not having the adsorbent functional group bound thereto.

Embodiment 77 provides the adsorbent catalyst of any one of Embodiments 64-76, wherein a percent selectivity of the adsorbent catalyst toward catalyzation of hydrodeoxygenation of a fatty acid is about 100% to about 800% of a selectivity toward catalyzation of hydrodeoxygenation of the fatty acid of a corresponding mesoporous silica nanoparticle including the catalytic material but not having the adsorbent functional group bound thereto.

Embodiment 78 provides the adsorbent catalyst of any one of Embodiments 64-77, wherein a percent selectivity of the adsorbent catalyst toward catalyzation of hydrodeoxygenation of a fatty acid is about 200% to about 600% of a selectivity toward catalyzation of hydrodeoxygenation of the fatty acid of a corresponding mesoporous silica nanoparticle including the catalytic material not having the adsorbent functional group bound thereto.

Embodiment 79 provides a catalyst comprising: a mesoporous silica nanoparticle comprising a pore size of about 5 nm to about 15 nm and a pore volume of about 0.5 to about 1.5 cm$^3$/g; and a catalytic material comprising iron nanoparticles having a particle size of about 5 nm to about 15 nm at least partially within pores of the mesoporous silica nanoparticle, the iron nanoparticles comprising about 1-10 wt % of the catalyst; wherein the catalyst has a surface area of about 150 m$^2$/g to about 375 m$^2$/g.

Embodiment 80 provides the apparatus or method of any one or any combination of Embodiments 1-79 optionally configured such that all elements or options recited are available to use or select from.

What is claimed is:

1. A method comprising:
  combining a catalyst with at least one first molecule comprising at least one of a fatty acid, a fatty acid ester, a monoglyceride, a diglyceride, and a triglyceride, to provide a mixture, the catalyst comprising a mesoporous silica nanoparticle comprising a catalytic material, the catalytic material comprises iron nanoparticles that are at least partially within pores of the mesoporous silica nanoparticle, wherein
  the catalyst is an adsorbent catalyst,
  the catalyst comprises at least one adsorbent functional group comprising a functional group selected from the group consisting of an amino($C_1$-$C_{20}$)alkyl group or a salt thereof, a ($C_1$-$C_{20}$)alkyl carboxylic acid group or a salt thereof, a ($C_1$-$C_{20}$)alkyl sulfonic acid group or a salt thereof, and a perfluoro($C_1$-$C_{20}$)alkyl group,
  the alkyl unit of the aminoalkyl group, the alkyl carboxylic acid group, the alkyl sulfonic acid group, and of the perfluoroalkyl group is covalently bound to the mesoporous silica nanoparticle, and
  the $C_1$-$C_{20}$ alkyl groups of the amino($C_1$-$C_{20}$)alkyl group are independently optionally interrupted by one or two —NH— groups; and
  combining the mixture with a hydrogen gas under conditions so that the catalytic material in the catalyst catalyzes a chemical transformation of the first molecule comprising hydrotreatment to form a hydrotreatment product, the chemical transformation comprising at least one of hydrogenation, reduction, decarboxylation, and hydrodeoxygenation of the first molecule, wherein the catalyzing of the chemical transformation comprises catalyzing of at least one of the hydrogenation, the reduction, the decarboxylation, and the hydrodeoxygenation at a higher rate than hydrocracking.

2. The method of claim 1, wherein the catalytic material has a particle size equal to or less than a pore size of the catalytic material.

3. The method of claim 1, wherein the catalytic material has a particle size of about 5 nm to about 15 nm.

4. The method of claim 1, wherein about 0.1 wt % to about 30 wt % of the catalyst is the catalytic material.

5. The method of claim 1, wherein the catalyst has a particle size of about 50 nm-1200 nm.

6. The method of claim 1, wherein the catalyst has a pore size of about 5 nm to about 15 nm.

7. The method of claim 1, wherein the first molecule is selectively adsorbed by the adsorbent functional group.

8. The method of claim 1, wherein the catalyst is sufficient to catalyze hydrocracking of a ($C_5$-$C_{50}$) fatty acid in the presence of $H_2$ such that, at about 100% conversion of the fatty acid, at a temperature of about 200° C. to about 400° C., about 0.01-15% of the yield of the reaction is hydrocracking product.

9. The method of claim 1, wherein the catalyst is sufficient to catalyze at least one of hydrogenation, reduction, decarboxylation, and hydrodeoxygenation of at least one of a $C_{5-50}$ fatty acid $C_{1-50}$ ester and a triglyceride having $C_{5-50}$ fatty acid groups in the presence of $H_2$ at a temperature of about 200° C. to about 400° C.

10. The method of claim 1, wherein the adsorbent functional group adsorbs fatty acids at a higher rate than it adsorbs at least one of fatty acid esters and triglycerides.

11. The method of claim 1, wherein the adsorbent functional group comprises at least one of an amino($C_{1-10}$)alkyl group and a salt thereof wherein the alkyl unit is covalently bound to the mesoporous silica nanoparticle.

12. The method of claim 1, wherein the adsorbent functional group is present in a concentration of about 0.01 mmol to about 50 mmol per gram of the mesoporous silica nanoparticle.

13. The method of claim 1, wherein the adsorbent catalyst is sufficient to catalyze decarboxylation and hydrodeoxygenation of a fatty acid at a higher rate than a corresponding mesoporous silica nanoparticle not having the adsorbent functional group bound thereto.

14. The method of claim 1, wherein:
the mesoporous silica nanoparticle comprises a particle size of about 50 nm to about 1200 nm, a pore size of about 5 nm to about 15 nm, and a pore volume of about 0.5 to about 1.5 $cm^3$/g,
the catalytic material comprises iron nanoparticles having a particle size of about 5 nm to about 15 nm at least partially within pores of the mesoporous silica nanoparticle, the iron nanoparticles comprising about 1-10 wt % of the catalyst, and
the catalyst has a surface area of about 150 $m^2$/g to about 375 $m^2$/g.

* * * * *